United States Patent
Bessler et al.

(10) Patent No.: US 10,743,857 B2
(45) Date of Patent: Aug. 18, 2020

(54) LUMEN REINFORCEMENT AND ANCHORING SYSTEM

(71) Applicant: ENDOBETES INC., New York, NY (US)

(72) Inventors: Marc Bessler, New Rochelle, NY (US); Ryan Hanlon, Hudson, NH (US); Zachary Tyler Melanson, Hudson, NH (US)

(73) Assignee: Endobetes, Inc., New York, NY (US)

( * ) Notice: Subject to any disclaimer, the term of this patent is extended or adjusted under 35 U.S.C. 154(b) by 0 days.

(21) Appl. No.: 16/046,592

(22) Filed: Jul. 26, 2018

(65) Prior Publication Data

US 2020/0029951 A1   Jan. 30, 2020

(51) Int. Cl.
| | | |
|---|---|---|
| *A61B 17/04* | (2006.01) | |
| *A61F 2/00* | (2006.01) | |
| A61B 17/064 | (2006.01) | |
| A61F 2/04 | (2013.01) | |
| A61F 5/00 | (2006.01) | |

(52) U.S. Cl.
CPC ........ *A61B 17/0401* (2013.01); *A61F 2/0063* (2013.01); *A61B 17/064* (2013.01); *A61B 2017/0409* (2013.01); *A61B 2017/0437* (2013.01); *A61F 2/04* (2013.01); *A61F 5/0036* (2013.01)

(58) Field of Classification Search
CPC .......................... A61B 17/0401; A61F 2/063
See application file for complete search history.

(56) References Cited

U.S. PATENT DOCUMENTS

| | | | |
|---|---|---|---|
| 5,843,164 A | | 12/1998 | Frantzen et al. |
| 6,004,347 A | * | 12/1999 | McNamara ............... A61F 2/07 606/194 |
| 6,036,725 A | * | 3/2000 | Avellanet ................. A61F 2/91 623/1.13 |
| 7,211,114 B2 | * | 5/2007 | Bessler ..................... A61F 2/07 623/23.65 |
| 7,837,645 B2 | | 11/2010 | Bessler et al. |
| 9,044,300 B2 | | 6/2015 | Belhe et al. |
| 9,398,969 B2 | | 7/2016 | Babkes |
| 9,402,720 B2 | | 8/2016 | Richter et al. |
| 9,775,728 B2 | | 10/2017 | Davis et al. |
| 2001/0020189 A1 | * | 9/2001 | Taylor ................... A61F 2/0004 623/23.68 |

(Continued)

FOREIGN PATENT DOCUMENTS

EP   1555970 B1   7/2005

OTHER PUBLICATIONS

Search Report and Written Opinion dated Dec. 19, 2019 for PCT/US2019/042801.

*Primary Examiner* — Richard G Louis
(74) *Attorney, Agent, or Firm* — Akerman, LLP

(57) ABSTRACT

A tissue wall of a biological lumen may be reinforced by embedding a material or structure into the tissue wall. The reinforcement material or structure may embed by application of outwardly directed force along an interior side of the tissue wall, threading, or injection. The reinforcement material or structure may act as an embedded scaffold that limits expansion or contraction of the tissue wall to pushing or pulling forces. An anchor device, such as a medical device, may anchor to the reinforced portion of the tissue wall.

26 Claims, 15 Drawing Sheets

(56) References Cited

U.S. PATENT DOCUMENTS

| | | | |
|---|---|---|---|
| 2002/0099437 A1* | 7/2002 | Anson | A61B 17/0057 623/1.15 |
| 2005/0010275 A1* | 1/2005 | Sahatjian | A61F 2/88 623/1.11 |
| 2005/0125075 A1* | 6/2005 | Meade | A61B 17/0401 623/23.64 |
| 2006/0025808 A1* | 2/2006 | Thompson | A61B 17/3478 606/204 |
| 2007/0055365 A1* | 3/2007 | Greenberg | A61F 2/01 623/1.44 |
| 2008/0269868 A1* | 10/2008 | Bei | A61F 2/013 623/1.11 |
| 2009/0048664 A1* | 2/2009 | Cage | A61F 2/86 623/1.36 |
| 2010/0256775 A1* | 10/2010 | Belhe | A61F 5/0076 623/23.65 |
| 2011/0004230 A1 | 1/2011 | Levine et al. | |
| 2011/0282368 A1* | 11/2011 | Swayze | A61B 17/00491 606/159 |
| 2012/0123514 A1* | 5/2012 | Kunis | A61F 2/88 623/1.11 |
| 2014/0309576 A1 | 10/2014 | Belhe et al. | |
| 2018/0000616 A1* | 1/2018 | Siersema | A61F 2/82 |

\* cited by examiner

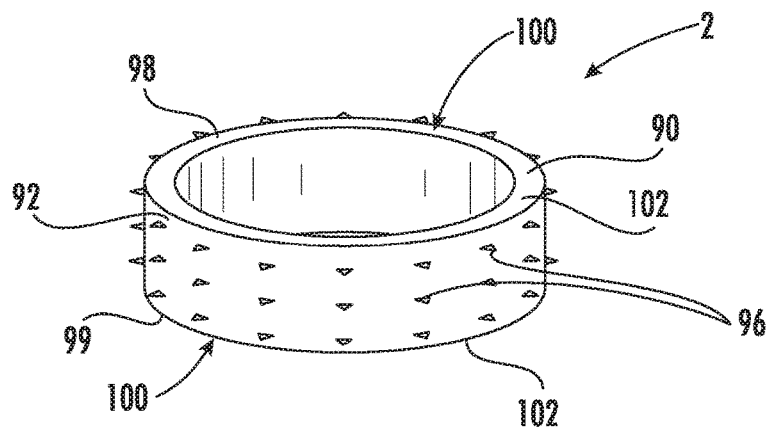
FIG. 9
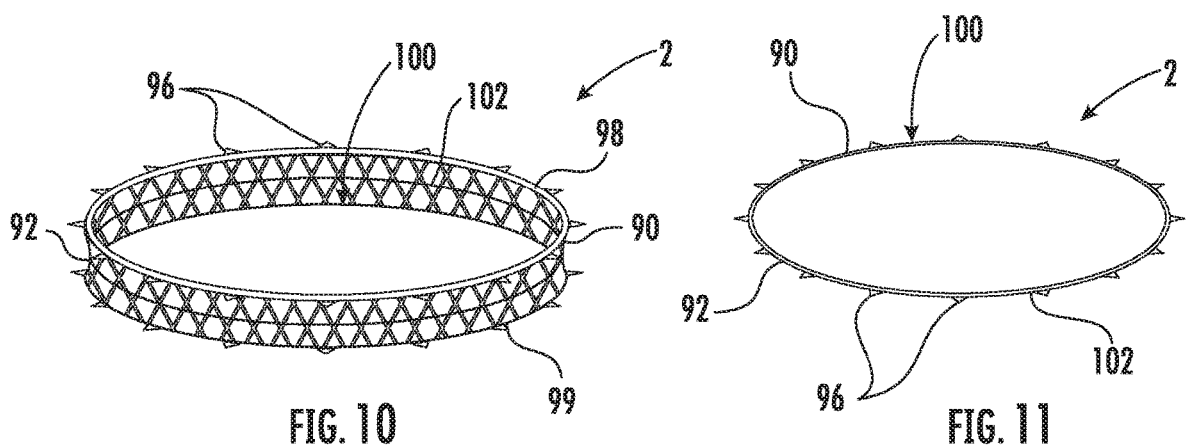
FIG. 10
FIG. 11
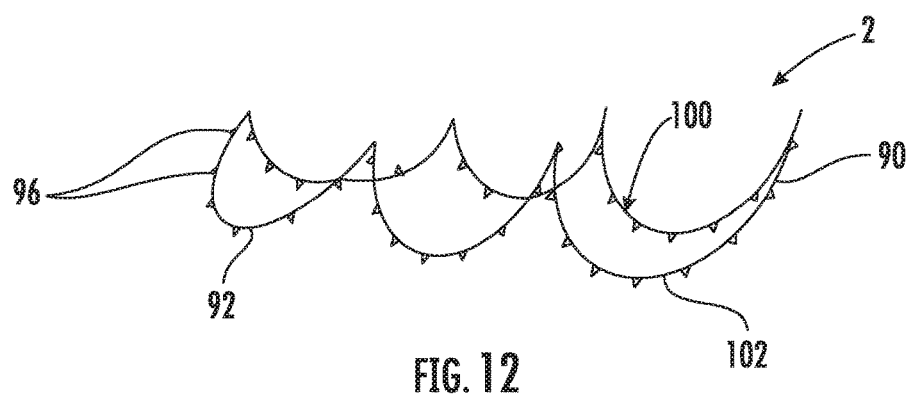
FIG. 12

LUMEN REINFORCEMENT AND ANCHORING SYSTEM

TECHNOLOGY FIELD

The present disclosure is directed to biological lumen reinforcement and anchoring systems and methods of anchoring devices within a biological lumen. The present disclosure is further directed to methods for reinforcing a tissue wall defining a biological lumen.

BACKGROUND

Medical devices may be implanted in biological lumens. Current surgical procedures for anchoring such devices include utilizing hooks to puncture through the wall of the lumen or otherwise internally anchoring the device via interaction external to the lumen. Such procedures, however, tend to be more complicated and present higher risk of negative outcomes and trauma to the patient. Implanted medical devices may also be subject to pushing or pulling forces due to normal function of the lumen or the device. These forces may result in anchored hooks tearing the tissue wall, causing further trauma and migration of the device from a target site.

Improved techniques for anchoring an implanted medical device are needed.

SUMMARY

In one aspect, a method of reinforcing a tissue wall of a biological lumen includes embedding a reinforcement material or structure into a portion of the tissue wall.

In various embodiments, the reinforcement material or structure may include an embedment device having a body. Embedding the reinforcement material or structure comprises delivering the embedment device into the lumen and applying outwardly directed force along an interior side of the tissue wall to embed the body therein.

In one example, the body of the embedment device has a cross-section dimension greater than a corresponding cross-section dimension of the lumen to therein apply the outwardly directed force along the interior side of the tissue wall. The cross-section dimension of the body may be less than a corresponding cross-section dimension of the tissue wall and corresponding lumen, taken from exterior sides of the tissue wall, such that the body does not migrate to an exterior side of the tissue wall. The body of the embedment device may include a wire coil or a wire mesh.

In another example, the body of the embedment device comprises an expandable tube. The expandable tube may be expandable or biased to obtain a cross-section dimension greater than a corresponding cross-section dimension of the lumen to therein apply the outwardly directed force along the interior side of the tissue wall. The expandable tube may include a wire mesh or coil.

In one example, the body comprises a wire mesh. The wire mesh may include one or more physical blocks extending between adjacent openings to prevent migration of the body to an exterior side of the tissue wall.

In another example, the body of the embedment device has an embedding conformation and an embedded conformation. The body may apply the outwardly directed force in the embedding conformation and discontinues application of the outwardly directed force in the embedded conformation. In the embedded conformation, a cross-section dimension of the body may be less than a corresponding cross-section dimension of the tissue wall and corresponding lumen, taken from exterior sides of the tissue wall, such that the body does not migrate to an exterior side of the tissue wall.

In another example, applying the outwardly directed force along an interior side of the tissue wall comprises compressing the reinforcement material or structure against the interior side of the tissue wall. Compressing the reinforcement material or structure against the interior side of the tissue wall may include positioning an inflatable device within the lumen and inflating the inflatable device such that the inflatable device obtains a cross-section sufficient to compress the reinforcement material or structure against the interior side of the tissue wall. In another example, the body includes one or more outwardly directed projections configured to penetrate, e.g., puncture, the tissue, wherein the projections are dimensioned to not puncture an exterior side of the tissue wall. In one embodiment, the projections may then be separated from the body thereby depositing them in the tissue wall once the embedment device has embedded the tissue wall. The projections may be absorbable or configured to disintegrate over time, for example. In some embodiments, a positioning device may be used to assist in embedding or maintaining positioning of the body of the embedment device during embedment. The positioning device may be expandable or biased outwardly to apply outward directed pressure and compress the body against the tissue wall, configured to apply inward directed force, such as suction or negative pressure, to pull the tissue wall inward, or may temporarily cover or anchor the embedment device to hold the embedment device in place, e.g., using barbs, hooks or pins. The positioning device may be removed when the embedment device has embedded the tissue wall.

In one embodiment, the body of the embedment device may be secured in position along the interior side of the tissue wall with a positioning device. The embedment device may be configured to increase a cross-section dimension to apply outward directed force, for example. The method may include delivering the positioning device into the lumen and positioning the positioning device within the lumen, interior of the material or structure, to secure the body of the embedment device along the interior side of the tissue wall during the embedding. The positioning device may include one or more projections to penetrate the tissue wall but not puncture an exterior side of the tissue wall. In one embodiment, the projections are attached to the body and comprise a projection selected from a dissolvable or absorbable barbs, hooks, or pins.

In an embodiment, the method includes delivering a positioning device into the lumen and positioning the positioning device within the lumen, interior of the material or structure, to secure the body of the embedment device along the interior side of the tissue wall during the embedding. The positioning device may include a body and one or more projections. The one or more projections may penetrate the tissue wall but not puncture an exterior side of the tissue wall. In one example, the body of the positioning device is absorbable or dissolvable. In one example, the method includes removing the positioning device after the embedment device has embedded the tissue wall. In one embodiment, the projections may be separated from the body thereby depositing the projections in the tissue wall when the material or structure is embedded into the portion of the tissue wall. For example, the projections may include an absorbable barb, hook, or pin. The body may then be removed.

In one embodiment, the body of the embedment device, e.g., the reinforcement material or structure, may be heated or an electrical current, continuous or pulse, may be conducted through it to assist in embedding the reinforcement material or structure into the portion of the tissue wall.

In some embodiments embedding the reinforcement material or structure comprises threading a wire along the portion of the tissue wall. In this or another embodiment embedding the reinforcement material or structure comprises injecting a polymer into the portion of the tissue wall.

In another aspect, a method of anchoring an anchor device to a tissue wall of a biological lumen includes anchoring the anchor device to a reinforced portion of the tissue wall wherein the reinforced portion of the tissue wall comprises a material or structure embedded in the reinforced portion of the tissue wall.

The anchor device may include a body having one or more outward facing projections extending along a perimeter of the body. The projections may penetrate, e.g., puncture, the portion of the tissue but do not puncture an exterior side of the tissue wall. The anchor device may apply outwardly directed force along the portion of the reinforced portion of the tissue wall. The anchor device may anchor to the reinforced portion of the tissue wall via magnetic attraction wherein the material or structure embedded in the reinforced portion of the tissue includes magnets or magnet attractive materials.

The material or structure embedded in the reinforced portion of the tissue may include a portion that extends within the lumen. The anchor device may include a body having one or more outward facing projections extending along a perimeter of the body. The projections may be positioned to engage the portion of the material or structure that extends within the lumen. In one example, the anchor device anchors to the reinforced portion of the tissue wall via magnetic attraction, and the portion of the material or structure that extends within the lumen includes a magnet or magnet attractive material.

In still another aspect, an anchoring system for anchoring to a tissue wall of a biological lumen includes a medical device comprising a gastric bypass sleeve; an anchor device positioned at a proximal end of the gastric bypass sleeve to anchor to a tissue wall in the esophagus; and a structure extending along the gastric bypass sleeve from the proximal end to a distal end to extend the gastric bypass sleeve from the esophagus, through the stomach, and position the distal end in the gastric bypass sleeve within the duodenum.

In some embodiments, the structure may be fixed in the gastric bypass sleeve. In one embodiment, the structure coils around the gastric bypass sleeve.

In various embodiments, the structure comprises a stiffening wire. The stiffening wire may comprise a fixed wire embedded in the gastric bypass sleeve. In one embodiment, the stiffening wire may coil around the gastric bypass sleeve. The stiffening wire coils may be bendable to define a path from the stomach into the duodenum.

In yet another aspect, an anchoring system for anchoring to a tissue wall of a biological lumen includes a medical device comprising a gastric bypass sleeve; a first anchor device positioned at a proximal end of the gastric bypass sleeve to anchor to a tissue wall in the esophagus; and a second anchor device positioned at a distal end of the gastric bypass sleeve to anchor the distal end within the duodenum, wherein the second anchor device comprises a body configured to anchor within the duodenum. This may be by application of outwardly directed force against the tissue wall or formation into a configuration that does not permit retrograde passage into the stomach.

In various embodiments, the anchor system further includes an embedment device to embed within a portion of the tissue wall of the esophagus in which the first anchor device anchors. The embedment device may include a structure selected from a mesh or coil having an embedding conformation wherein the structure is biased to a cross-section dimension greater than a corresponding cross-section dimension of esophagus to apply outwardly directed force along the portion of the tissue wall of the esophagus in which the first anchor device anchors.

In one embodiment, the first anchor system also includes a body having projections positioned along an outer perimeter to puncture the tissue along the portion of the tissue wall of the esophagus in which the first anchor device anchors. In this or another embodiment, the embedment device comprises a polymer for injection or wire for threading along the portion of the tissue wall of the esophagus in which the first anchor device anchors. The first anchor device may include a body having projections positioned along an outer perimeter to puncture the tissue along the portion of the tissue wall of the esophagus in which the first anchor device anchors.

In one embodiment, the anchor system also includes an embedment device to embed within a portion of the tissue wall of the duodenum in which the second anchor device anchors. The embedment device may include a structure selected from a mesh or coil having an embedding conformation wherein the structure is biased to a cross-section dimension greater than a corresponding cross-section dimension of duodenum to apply outwardly directed force along the portion of the tissue wall of the duodenum in which the second anchor device anchors. The body of the second anchor device may include a doughnut or hollow cylinder shaped balloon. The embedment device may include a polymer for injection or wire for threading along the portion of the tissue wall of the duodenum in which the second anchor device anchors.

In still yet another aspect, a method of preventing dilation of a biological lumen includes embedding a material or structure into a portion of a tissue wall defining the lumen. The material or structure may have a maximum cross-section dimension or perimeter corresponding to an allowable degree of dilation of the lumen.

In various embodiments, the material or structure comprises an embedment device having a body. Embedding the material or structure may include delivering the embedment device into the lumen and applying outwardly directed force along an interior side of the tissue wall to embed the body therein. In one embodiment, the body comprises a maximum cross-section dimension. The maximum cross-section dimension may be less than a corresponding cross-section dimension of the tissue wall and corresponding lumen, taken from exterior sides of the tissue wall, such that the body does not migrate to an exterior side of the tissue wall. In one example, the body of the embedment device comprises a wire coil or a wire mesh.

In one embodiment, the body of the embedment device comprises an expandable tube. The expandable tube may comprise a wire mesh or coil, for example.

In some embodiments, the body of the embedment device may have an embedding conformation and an embedded conformation. The body may apply the outwardly directed force in the embedding conformation and discontinue application of the outwardly directed force in the embedded conformation. In the embedded conformation, a cross-section dimension of the body may be less than a corresponding cross-section dimension of the tissue wall and corresponding lumen, taken from exterior sides of the tissue wall, such that the body does not migrate to an exterior side of the tissue wall.

In various embodiments, applying the outwardly directed force along an interior side of the tissue wall comprises compressing the material or structure against the interior side of the tissue wall. Compressing the material or structure against the interior side of the tissue wall may comprise positioning an inflatable device within the lumen and inflating the inflatable device such that the inflatable device obtains a cross-section sufficient to compress the reinforcement material or structure against the interior side of the tissue wall.

In some embodiments, compressing the material or structure against the interior side of the tissue wall comprises applying a suction or negative pressure within the lumen.

In one embodiment, the body may be secured in position along the interior side of the tissue wall with a positioning device. The method may include delivering the positioning device into the lumen and positioning the positioning device within the lumen, interior of the material or structure, to secure the body of the embedment device along the interior side of the tissue wall during the embedding. The positioning device may include one or more projections to penetrate the tissue wall but not puncture an exterior side of the tissue wall. In one embodiment, the projections are attached to the body and comprise a projection selected from a dissolvable or absorbable barbs, hooks, or pins.

In an embodiment, the method includes delivering a positioning device into the lumen and positioning the positioning device within the lumen, interior of the material or structure, to secure the body of the embedment device along the interior side of the tissue wall during the embedding. The positioning device may include a body and one or more projections. The one or more projections may penetrate the tissue wall but not puncture an exterior side of the tissue wall. In one example, the body of the positioning device is absorbable or dissolvable. In one example, the method includes removing the positioning device after the embedment device has embedded the tissue wall. In one embodiment, the projections may be separated from the body thereby depositing the projections in the tissue wall when the material or structure is embedded into the portion of the tissue wall. For example, the projections may include an absorbable barb, hook, or pin. The body may then be removed.

In some embodiments, embedding the material or structure may be assisted by heating or conducting an electrical current through the material or structure to assist in embedding the material or structure into the portion of the tissue wall. In one embodiment, embedding the material may be assisted by dimensions of the material or structure favorable for embedding, e.g., a leading edge or wedge, oriented toward the tissue wall. In some embodiments, embedding may be assisted by biological or chemical treatments. For example, the material or structure may include or be coated or enveloped by an acid to disrupt the tissue lining the tissue wall.

In some embodiments, the body includes one or more outwardly directed projections configured to penetrate, e.g., puncture, tissue. The projections may be dimensioned to not puncture an exterior side of the tissue wall.

In one embodiment, the material or structure comprises threading a wire along the portion of the tissue wall. In this or another embodiment, embedding the material or structure comprises injecting a polymer into the portion of the tissue wall.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

FIG. 9 illustrates an anchor device according to various embodiments described herein;

FIG. 10 illustrates an anchor device according to various embodiments described herein;

FIG. 11 illustrates an anchor device according to various embodiments described herein;

FIG. 12 illustrates an anchor device according to various embodiments described herein;

DESCRIPTION

Figure 1:
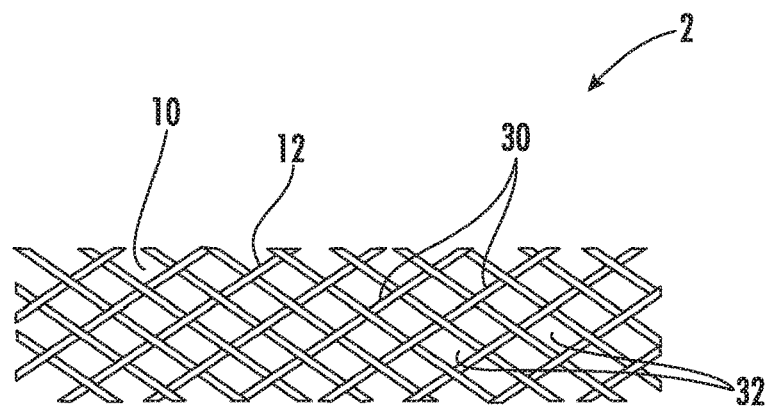
FIG. 1 illustrates an embedment device according to various embodiments described herein.

Anchoring systems and associated devices and methods of anchoring devices within biological lumens which may include reinforcing a tissue wall defining a biological lumen are described herein.

The anchoring systems and associated devices and methods described herein may be used to anchor devices. The devices anchored may include medical devices or platforms for coupling to medical devices to be anchored within a biological lumen. The medical devices may include diagnostic, therapeutic, regulatory, sensors, separation, transport, or other devices. For example, anchor devices or devices that may be coupled to an anchored platform may include medical devices that regulate or modify flow of material within the lumen, detect or analyze components of material within the lumen, release of substances into the lumen such as medications or other therapeutic substances, or observe or measure conditions or state within the lumen.

In some embodiments, an anchoring system includes an embedment device configured to embed a tissue wall defining a biological lumen. The embedment device may strengthen a tissue wall. For example, an embedment device may include a structure that embeds the tissue wall and thereby reinforces the tissue wall. The embedment device may be configured to maintain a dimension or range of dimension with respect to the lumen. For example, the embedment device may limit a cross-section dimension such as a diameter or circumference of the lumen, which may include maintaining an overall cross-section shape of the lumen. Thus, an embedment device may prevent a lumen from increasing or decreasing beyond a cross-section dimension such as diameter or circumference, which may include deformation of a cross-section shape. In one example, an embedment device prevents a stomach from expanding after gastric reduction surgery. In another example, an embedment device prevents esophageal dilation in patients with Achalasia.

In various embodiments, an anchoring system includes a self-expanding embedment device to push into a tissue wall to embed therein. In some embodiments, the embedment device comprises a body having a generally tubular configuration. The embedment device may be configured to not embed too deep within the wall. For example, migration of the embedment device through the tissue wall may be prevented by a maximum dimension or perimeter defined by the device or a physical block. A positioning device may be used to accelerate the embedment process or assist in retaining the position of the embedment device until embedded. An anchor device may anchor to the embedded device by penetrating tissue or by engaging a projection of the embedment device within the lumen.

In various embodiments, an anchoring system includes an anchor device configured to stably anchor within a biological lumen. An embedment device may be used to reinforce and strengthen a tissue wall to assist in anchoring of the anchoring device. The anchor device may anchor along or adjacent to one or more reinforced portions of a wall defining the biological lumen. For example, an anchor device may anchor within a lumen by application of outwardly directed force along a reinforced portion of a tissue wall. The embedment device may prevent the tissue wall from expanding away from the outwardly directed force and thereby improve grip from the outwardly directed force. In some embodiments, an anchor device may anchor within a lumen utilizing projections such as hooks that engage the embedded structure or penetrate, e.g., puncture, into reinforced tissue. As described in more detail below, other arrangements for anchoring an anchoring device may be used, such as incorporating magnets.

In some embodiments, the anchoring system includes an anchor device that comprises a medical device. In these or other embodiments, the anchoring system includes an anchor device that comprises a platform to couple a medical device. Such a modular configuration may allow utilization of the anchor device as a platform for implanting and removing devices to be anchored by the anchor device. Anchor devices that include or incorporate medical devices may similarly be configured to utilize the embedment device as a platform for implanting and removing the medical device having the integrated anchoring device platform. In still further embodiments, the embedment device includes anchoring structures configured to couple to an anchor device.

The anchor system is generally described herein with respect to dimension control, reinforcement, anchoring, and combinations thereof within the gastrointestinal tract; however, the anchor system may find use with respect to other lumens and tissue walls defining such lumens. For example, various embodiments of the anchor system, which may include associated devices and methods thereof, may be applied to control dimensions, reinforce, or anchor devices within tissue defining a biological lumen, which may include embedding a structure within a tissue wall, selected from a lumen within the vascular system, artery, vein, gastrointestinal tract, esophagus, cardia, stomach, pylorus, small or large intestines, duodenum, colon, rectum, urinary tract, bladder, prostate, urethra, reproductive system, vagina, uterus, fallopian tubes, respiratory system, larynx, or bronchi, for example.

With reference to FIGS. 1-8, illustrating embedment devices 10 according to various embodiments described herein, an anchor system 2 may include an embedment device 10. The embedment device 10 may include a body 12. The body 12 may comprise a rigid structure, flexible structure, injected polymer, threaded wire, as examples, configured to reinforce or strengthen a biological lumen. In one embodiment, the body may be rigid with respect to expansion of a cross-section greater than a maximum cross-section to limit dilation of a lumen but may be collapsible or resiliently collapsible to allow contraction of a lumen. In some embodiments, the body 12 may comprise a generally tubular structure. As introduced above, some embodiments of an embedment device 10 are dimensioned to apply outwardly directed force along a tissue wall. The outwardly directed force may result in all or a portion of the body 12 embedding in the tissue wall. The portion of the body that embeds may be referred to as an embedded structure of the body.

Figure 23:
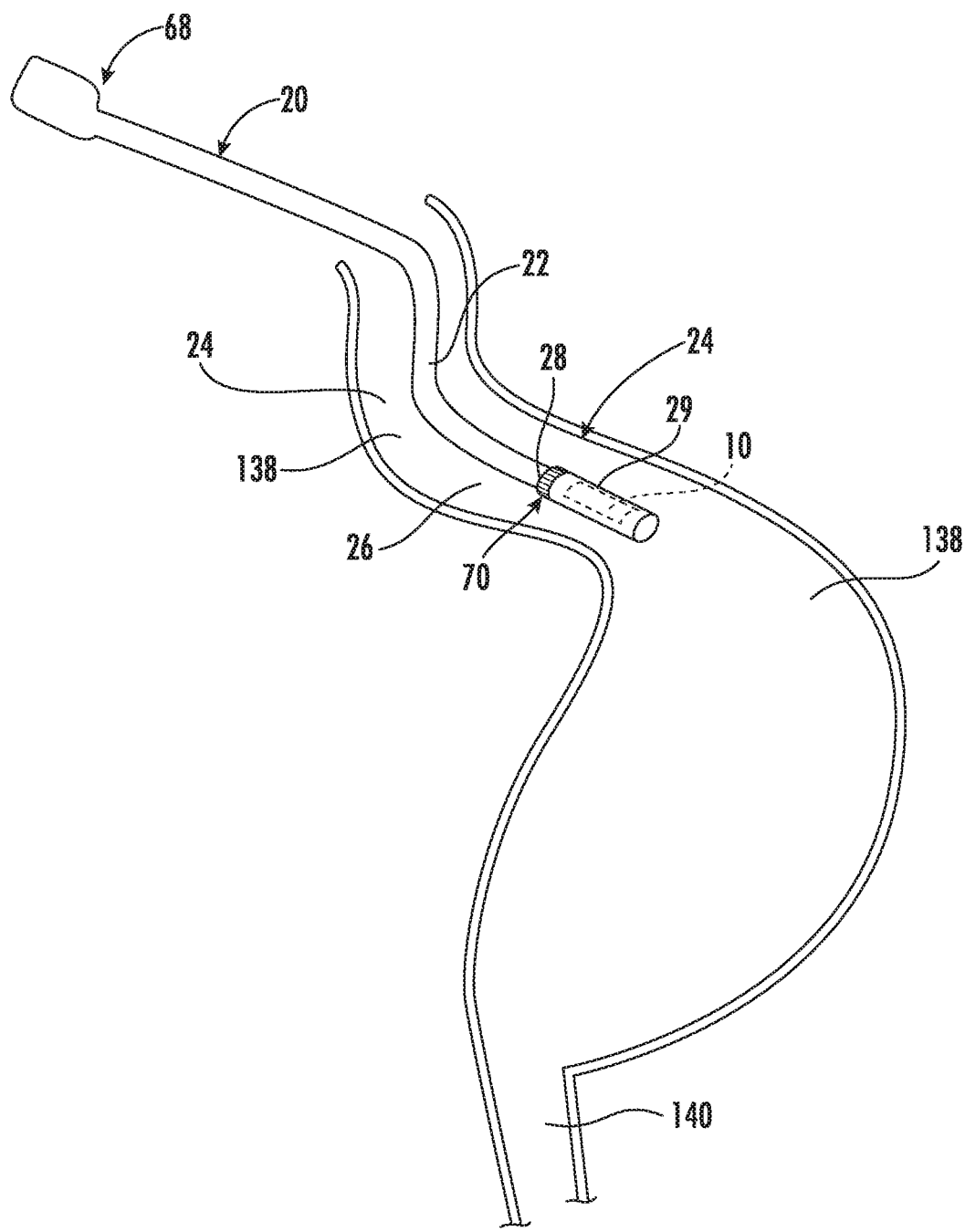
FIG. 23 illustrates a method of implanting an embedment device according to various embodiments described herein.
Figure 24A:
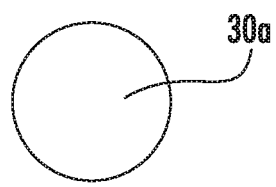
FIGS. 24A-24D illustrate example cross-section shapes of wires according to various embodiments wherein FIG. 24A includes a round cross-section shape, FIGS. 24B & 24D include quadrilateral cross-sections shapes, and FIG. 24C includes a wedge cross-section shape.
Figure 24B:
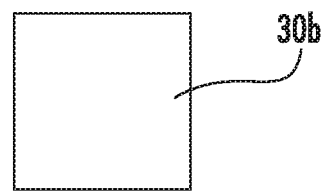
Figure 24C:
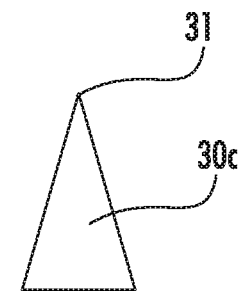
Figure 24D:
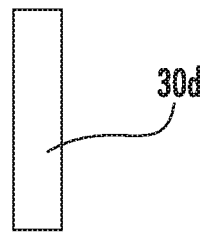

In various embodiments, the body 12 may be biased to expand outwardly or to an increased diameter than that of the lumen into which it reinforces. In some embodiments, the force is due to a dimension of the lumen being less than a corresponding dimension of the body 12 resulting in the restricted dimension, such as diameter, of the lumen causing conformational stress along the corresponding dimension of the body 12. The conformational stress may result in application of outward force onto the lumen wall. The body 12 may be biased to expand to a predetermined maximum embedded dimension. In some embodiments, the body 12 obtains a dimension when implanted in the lumen, forcing the lumen to obtain the greater corresponding dimension of the body 12. The dimension obtained by the body 12 may correspond to its maximum embedded dimension. In either instance, the force applied by the body 12 drives embedment of the body 12 into the lumen to reinforce the lumen. In various embodiments, the maximum embedded dimension of the body 12 may be between approximately 0.5 mm and approximately 1 cm larger than the corresponding diameter of the lumen when implanted. In one example, the diameter of the body 12 is between approximately 1 mm and approximately 5 mm, such as between approximately 1 mm and approximately 3 mm, larger than the corresponding diameter of the lumen. In some embodiments, outward directed force may be substantially evenly applied by the body 12 along the lumen. In other embodiments, force may be differentially applied. With further reference to FIG. 23, delivering the embedment device 10 to a target site 24 may include delivery utilizing endoscopy and fluoroscopy together with an endoscopic delivery device 20. For example, the delivery device 20 may include an endoscopic catheter. In one application, the embedment device 10 may be delivered using a wire guided catheter. The embedment device 10, for instance, may be collapsed and inserted into a sheath 22. The catheter may be positioned under fluoroscopy to the target site 24 within the biological lumen 26. A plunger 25 may be used to urge the embedment device 10 from the sheath 22. The delivery device 20 or a similar delivery device may be used to deliver other devices, such as an anchor device.

To assist in delivery of the embedment device 10 to a target site 24 within a biological lumen, various embodiments of the embedment device 10 may comprise a delivery conformation wherein the body 12 is reduced in one or more dimensions for delivery. The delivery device 20 may couple, e.g., attach, hold, or retain, the embedment device 10 for delivery to the target site 24. In some embodiments, the anchor system 2 includes a retainer 29 configured to retain the embedment device 10 in the delivery conformation during delivery to the target site 24. The retainer 29 may be a mechanical retention device such as one or more clamps, latches, calipers, articulators, compressors, pockets or slots, such as those defining restrictive volumes configured to mechanically retain the embedment device 10 in the delivery conformation. In the example delivery device 20 illustrated in FIG. 23, the retainer 29 comprises a restrictive volume along a distal portion of the sheath 22. In some embodiments, a retainer separate from a delivery device 20 may be used in addition to or instead of a retainer 29 associated with a delivery device 20. For example, a retainer 29 may include one or more brackets, tubes, braces, cuffs, or clamps configured to retain the embedment device 10 in the delivery configuration. The delivery device 20 may release the embedment device 10 at the target site 24. Releasing the embedment device 10 may also release the retainer 29. In some embodiments, the delivery device 20 or another delivery device is configured to remove the retainer 29. As described in more detail below, the embedment device 10 may include a shape change or shape memory material. In some such embodiments, the embedment device 10 may not be mechanically retained in the delivery conformation during delivery. The delivery device 20 or another device may be used to encourage or drive expansion of the embedment device 10 to the embedding conformation at the target site 24 such that the expanded configuration of the embedment device 10 applies outwardly directed force to the walls surrounding the lumen 26 to encourage embedment of the embedment device 10.

With continued reference to FIGS. 1-8, as introduced above, the body 12 may be configured to increase a cross-section dimension. For example, the body 12 may increase a cross-section of the body 12 from a first cross-section dimension to a second cross-section dimension. The first cross-section dimension may correspond to the cross-section of the body 12 in the delivery conformation or the embedding conformation. The second cross-section dimension may correspond to the cross-section of the body 12 in the embedding conformation or the embedded conformation. The body 12 may be delivered into a lumen. Therein the body 12 may be initiated or biased to increase the cross-section. For example, the body 12 in the delivery or embedding conformation may include the first cross-section dimension and may be biased to obtain the second cross-section dimension.

In various embodiments, the body 12 may increase or be biased to increase the cross-section in the embedding conformation from the first cross-section dimension, which may correspond to the delivery conformation or an intermediate conformation, to the second cross-section dimension. The second cross-section dimension may be greater than the corresponding cross-section dimension of the lumen such that the body 12 applies outward force onto the tissue wall of the lumen either when the second cross-section is obtained or during the transition to the second cross-section dimension. In one example, the second cross-section dimension corresponds to the embedded conformation and the body 12 may quickly embed the tissue wall in the embedding conformation. It will be appreciated that the embedding conformation may be a transitional conformation wherein the cross-section is increasing or may correspond to the embedded conformation wherein the body 12 has obtained a cross-section greater than the corresponding lumen to therein embed. For example, the embedding conformation may include the body 12 transitioning the cross-section from the first cross-section dimension to the second cross-section dimension. In one embodiment, the second cross-section dimension is the maximum cross-section dimension the body 12 is configured to expand. In one example, the body 12 may embed the tissue wall prior to obtaining the second cross-section dimension and the embedded conformation comprises a cross-section dimension intermediate of the first and second cross-section dimensions.

With specific reference to FIG. 1 an example embedment device 2 may include a body 12 comprising a mesh structure, such as a wire mesh or weave of a plurality of intersecting or overlaid wires 30 defining openings 32 therebetween. The mesh structure may be dimensioned to contact and exert force, energy, a chemical or biologic interaction with one or more portions of tissue defining a biological lumen and therein embed to reinforce the wall. In some examples, the wires 30 forming the mesh may have a diameter of between approximately 0.001 and approximately 1 mm, such as approximately 0.01 mm. In some embodiments, larger or smaller diameter wire 30 may be used. In various embodiments, the wires 30 may be arranged to form linear or rounded sides that define the openings 32. For example, wires 30 may be arranged to define openings 32 having geometric or non-geometric shapes, such as circles, ovals, triangles, trapezoids, diamonds, squares, rectangles, hexagons, or other multi-sided shapes or free form, which may include multiple shapes, sides, sizes, of openings 32 along the body 12. The openings 32 defined by the wires 30 mesh may have a largest dimension greater than the diameter of wire 30 defining the opening. In the illustrated example, the wires 30 define openings 32 having a general diamond shape.

The body 12 may have any suitable shape. For example, the body 12 may include an outwardly positioned structure or wall that extends along a perimeter of the body 12 and include an inner opening or lumen. The opening may be defined by the outwardly positioned structure or wall or may be defined by other structures positioned inwardly of the outwardly positioned structure or wall. In various embodiments, the body 12 comprises a tubular structure. In some examples, the body 12 may have a cross-sectional shape corresponding to a cross-sectional shape of the lumen for which it is to reinforce. In some embodiments, the body 12 may be similar to a wire mesh stent having a general arcuate shape, such as a cylindrical or tubular shape, and that defines a generally arcuate opening. In some examples, the body 12 may have a cross-sectional shape having a diameter greater than a diameter of the lumen it embeds at one or more cross-section locations. For example, the diameter of the body 12 may be between approximately 0.5 mm and approximately 1 cm larger than the corresponding diameter of the lumen. In one example, the diameter of the body 12 is between approximately 1 mm and approximately 5 mm larger than the corresponding diameter of the lumen. While a single mesh layer is illustrated in FIG. 1, in some embodiments, an embedment device may comprise a body having multiple layers for embedding within a tissue wall.

In various embodiments, the body 12 may be between about 20 to about 45 mm in diameter. In these or another embodiment, the body 12 may be between about 30 and about 55 mm in length or more. Such dimensions may find use in gastrointestinal tract applications, for example. In some embodiments wherein the embedment device 10 is intended for vascular applications or other applications, the body 12 may have a diameter less than 30 mm, such as less than 5 mm. The length of the body 12 may also be less than 40 mm. Some embodiments may include a body 12 having a diameter less than 30 mm and a length less than 40 mm or greater than 55 mm. Other embodiments may include a body 12 having a diameter less than 30 mm and a length greater than 40 mm or greater than 50 mm. Still yet other embodiments may include a body 12 having a diameter greater than 45 mm and a length less than 40 mm or greater than 55 mm.

The wires 30 may comprise metal, alloy, or polymer wire sufficiently rigid to apply outwardly directed force at one or more locations along a tissue wall of a lumen when in an embedding conformation. The force applied to the wall may encourage embedment of the body 12 within the wall. As noted above and elsewhere herein, in some embodiments, the body 12 includes an expandable mesh or a spiral waveform.

In some embodiments, the dimensional extent the outwardly directed force is provided may be limited. For example, the body 12 may be configured to provide outwardly directed force in the embedding conformation until the body 12 has obtained a predetermined size dimension or embedded conformation. For instance, the body 12 may be configured to apply an outwardly directed force in an embedment conformation until a dimension of the body 12 has expanded to a predetermined size, which may be greater than a corresponding dimension of the lumen. The predetermined size may correspond to an embedded conformation. For example, the diameter of the body 12 in the embedded conformation may be between approximately 0.5 mm and approximately 1 cm larger than the corresponding diameter of the lumen. In one example, the diameter of the body 12 in the embedded conformation is between approximately 1 mm and approximately 5 mm larger than the corresponding diameter of the lumen.

The body 12 may comprise a material or configuration that may be compressed or otherwise reduced, e.g., deformed, in one or more dimensions in a delivery conformation for delivery to a target site, see, e.g., FIG. 23. Wires 30 may comprise a polymer, metal, or alloy, such as stainless steel, that may be delivered to a target site in a lumen in a resiliently compressed configuration. For example, the body 12 may be extended in length, which may reorient wires 30 to reduce a diameter or width dimension of the body 12 for delivery. The compressed delivery conformation may be applied by a delivery device that retains the body 12 in the compressed configuration either directly or indirectly, see, e.g., FIG. 23. The body 12 may be compressed in diameter or deformed for delivery to the target site as explained above and elsewhere herein. For example, a delivery device may include a tube or cannula that retains the body 12 in a delivery conformation having one or more reduced dimensions. At the target site, the delivery device may remove the retention to allow the body 12 to resiliently expand or reorient toward and against the tissue wall in the embedding conformation and thereon apply outwardly directed force.

In some embodiments, wires 30 comprise nitinol or other shape memory or shape change material configured to be delivered to the target site in a delivery conformation comprising a relaxed configuration, strained configuration, deformed configuration, compressed configuration or another configuration wherein the body 12 comprises one or more reduced dimensions. At the target site the body 12 may transition to the embedding conformation. The transition may result upon removal of a deforming force or due to an environmental condition at the target site or upon introduction of a shape change queue or condition introduced within the lumen or externally directed to the lumen. For example, chemical, heat, pH, magnetic, electric, or electromagnetic field queues, may be employed to initiate a conformational change. The conformational change may result in the body 12 applying outwardly directed force along one or more locations of the tissue wall defining the lumen. The body 12 may subsequently embed within the wall.

In some embodiments, the embedment device 10 may comprise other structures. For example, the embedment device 10 may comprise one or more rings. The rings may be separate or connected, such as in a coil configuration or a plurality of rings separated by one or more connecting members, such as wires, along one or more positions along the circumference of the rings.

Figure 2:
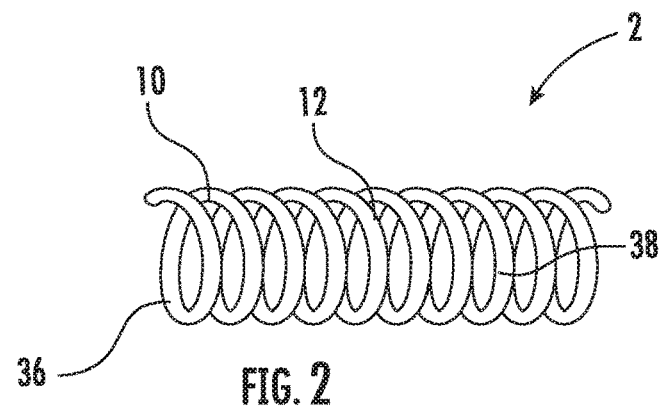
FIG. 2 illustrates an embedment device according to various embodiments described herein.

FIG. 2 illustrates an embedment device 10 comprising a body 12. The body 12 comprises a generally tubular structure having a helical configuration to various embodiments described herein. The body 12 comprises a plurality of annular rings 36 arranged in a helical configuration. For example, the body 12 may comprise coiled wire 38 in an embedding and/or embedded conformation.

The helical structure of the body 12 may be formed from materials as described above and elsewhere herein, e.g., materials described with respect to the mesh structure of the body 12 of the embedment device shown in FIG. 1. For example, the coiled wire 38 may comprise metal, alloy, or polymer wire sufficiently rigid to apply outwardly directed force at one or more locations along a tissue wall of a lumen when in an embedding conformation. The force applied to the wall may encourage embedment of the body 12 within the wall. In some embodiments, the dimensional extent the outwardly directed force is provided may be limited. For example, the body 12 may be configured to provide outwardly directed force in the embedding conformation until the body 12 has obtained a predetermined size dimension or embedded conformation. For instance, the body 12 may be configured to apply an outwardly directed force in an embedment conformation until a dimension of the body 12 has expanded to a predetermined size, which may be greater than a corresponding dimension of the lumen. The predetermined size may correspond to an embedded conformation.

The body 12 may comprise a material or configuration that may be compressed or otherwise reduced in one or more dimensions in a delivery conformation for delivery to a target site, see, e.g., FIG. 23. The coiled wires 30 may comprise a polymer, metal, or alloy, such as stainless steel, that may be delivered to a target site in a lumen in a resiliently compressed configuration. For example, the body 12 may be extended or reduced in length, which may reorient rings 36 to reduce a diameter, width, or thickness dimension of the body 12 for delivery. In one embodiment, the embedment device 10 may be delivered with the coiled wire 38 rings 36 resiliently compressed wherein the rings 36 are reoriented at the target site to extend along the lumen and therein apply outwardly directed force to the wall. In one embodiment, the coiled wire 38 may be resiliently extended in length, thereby reducing the diameter of the rings 36 for delivery to the target location. Once positioned at the target location, the coiled wire 38 may be released by the delivery device. As noted above, the delivery device may mechanically retain the coiled wire 38 in a compressed, extended, deformed, or other configuration either directly or indirectly wherein the body 12 or rings 36 thereof are reduced in one or more dimension. For example, a delivery device may include a tube or cannula that retains the body 12 in a delivery conformation having one or more reduced dimensions, which may be similar to the delivery device described with respect to FIG. 23. In one example, the delivery device may include a retainer comprising a clamp that physically restrains the coiled wire 38 from reobtaining one or more dimensions in which the body 12 has been reduced in the delivery conformation. At the target site, the delivery device may remove the retention to allow the coiled wire 38 to resiliently expand or reorient toward and against the tissue wall and thereon apply outwardly directed force in an embedding conformation. As described above with respect to FIG. 1, the body 12 may be between approximately 0.5 mm and approximately 1 cm larger than the corresponding diameter of the lumen. In one example, the diameter of the body 12 is between approximately 1 mm and approximately 5 mm, such as between approximately 1 mm and approximately 3 mm, larger than the corresponding diameter of the lumen. The body 12 may similarly be biased to a diameter greater than the lumen. For example, the body 12 may be biased in an embedding confirmation to an embedded conformation between approximately 0.5 mm and approximately 1 cm larger than the corresponding diameter of the lumen, such as between approximately 1 mm and approximately 5 mm or between approximately 1 mm and approximately 3 mm.

In some embodiments, the coiled wire 38 comprises nitinol or other shape memory or shape change material configured to be delivered to the target site in a delivery conformation comprising a relaxed configuration, strained configuration, deformed configuration, compressed configuration or another configuration wherein the body 12 comprises one or more reduced dimensions. At the target site the body 12 may transition to the embedding conformation. The transition may result upon removal of a deforming force or due to an environmental condition at the target site or upon introduction of a shape change queue or condition introduced within the lumen or externally directed to the lumen. For example, chemical, heat, pH, magnetic, electric, or electromagnetic field queues, may be employed to initiate a conformational change. The conformational change may result in the body 12 applying outwardly directed force along one or more locations of the tissue wall defining the lumen. The body 12 may subsequently embed within the wall.

Figure 3:
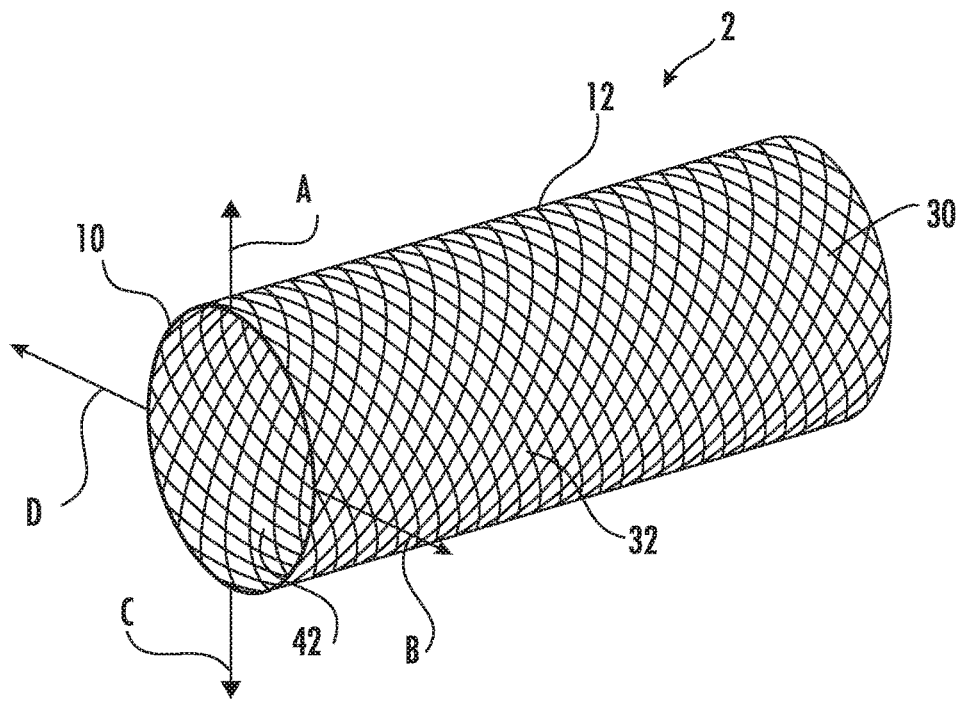
FIG. 3 illustrates an embedment device according to various embodiments described herein.

FIG. 3 illustrates an embodiment of an embedment device 10 wherein the body 12 has a generally tubular structure comprising expandable tubing 42. The expandable tubing 42 includes a mesh similar to FIG. 1 and includes wires 30 defining openings 32. The expandable tubing 42 is illustrated in an embedding conformation. In the embedding conformation, the expandable tubing 42 may be biased to expand outward, as indicated by arrows A, B, C, and D. In some examples, the expandable tubing may be biased outwardly differentially in one or more directions such that peripheral regions corresponding to one or more diameters apply greater force and/or apply force to a greater extent than peripheral regions corresponding to other diameters. In some examples, substantially equivalent outward directed force is applied about the perimeter in the embedding conformation. In some embodiments, the outward force may result in the lumen initially obtaining the cross-section of the expandable tubing 42. The expandable tubing 42 may embed the lumen wall. The expandable tubing 42 may embed the wall and include a maximum dimension, which may correspond to the embedded conformation, which in some examples may also correspond to the dimensions of the embedding conformation.

As introduced above, in some embodiments the body 12 may be between approximately 0.5 mm and approximately 1 cm larger than the corresponding diameter of the lumen. In one example, the diameter of the body 12 is between approximately 1 mm and approximately 5 mm larger than the corresponding diameter of the lumen. The body 12 may similarly be biased to a diameter greater than the lumen. For example, the body 12 may be biased in an embedding confirmation to an embedded conformation between approximately 0.5 mm and approximately 1 cm larger than the corresponding diameter of the lumen, such as between approximately 1 mm and approximately 5 mm.

An embedded system for attaching and holding an anchoring device in a biological lumen, such as the GI tract, may include an embedment device 10 having a body 12. The anchor device, for example, may hook onto an embedded structure of the body 12 as described herein. In some embodiments, the embedded structure may be an injected material or threaded wire. The anchoring device may hook into tissue a limited distance and engage the embedded structure. In another example, the anchoring device may engage a projection of the embedded structure that projects into the lumen. For instance, the body 12 may only partially embed a tissue wall such that a portion of the body 12 projects into the lumen. The projection structures may provide anchor points onto which the anchor device may engage to anchor within the lumen. As described in more detail elsewhere herein, the engagement may include hooks or magnets or other engagement or mating structures for coupling or adhesives, for example.

The embedded device 10 may reinforce the tissue wall limiting dilation, longitudinal movement, or both, of an anchoring device, which may include a medical device or may further anchor to a medical device.

The embedment device 10 may apply outward directed force to embed into the tissue wall defining the lumen or may be compressed against the tissue wall. In some embodiments, the embedment device 10 comprises a self-expanding body 12. The self-expanding body may have an expanding cross-section as described herein with respect to the examples and embodiments.

A method of embedding a structure or material into the wall of a GI tract to strengthen the wall, prevent dilation, and/or anchor other devices in a manner that may resist forces, such as outward, linear/longitudinal, or both may include embedding an embedment device 10 as described herein.

In various embodiments, the embedment device 10 may comprise a body 12 having additional or other configurations. As introduced above, the embedment device 10 may include a body 12 having an expandable dimension to transition from a delivery conformation to an embedding conformation, to apply force against a tissue wall in an embedding conformation, or both. The dimension may be expanded upon release of a retaining or compressing force or upon application of a conformational change queue, as described above. In further embodiments, the body 12 may be expanded utilizing a positioning device configured to expand a dimension of the body 12. In one example, the body 12 may be lined with or associable with a positioning device comprising a shape change or shape memory material configured to increase a dimension of the body 12 in the lumen. In some embodiments, a body 12 comprising an expandable dimension includes a wire coil, elastic wire, rolled wire sheet, e.g., mesh sheet, structures attached by elastic or loose wire, which may include thread.

In some embodiments, a positioning device may be configured to secure a position of the embedment device 10 during embedment of the embedment device 10. The positioning device may include projections such as hooks, barbs, pins, or other anchors for engaging tissue. The projections may be dissolvable or absorbable to disintegrate after the embedment device 10 has embedded the tissue wall. The projections may be attached to the embedment device 10 in some embodiments. In another embodiment, the positioning device comprises a body and one or more projections. The body may include structures to secure the position of the embedment device 10 during embedment. For example, the body may include a generally tubular structure such as a mesh. The body may include wires or surfaces for positioning interior of the embedment device within the lumen to hold the embedment device in place. In some embodiments, a positioning device may further include projections such as hooks, barbs, pins, or other tissue engaging anchors as noted above and elsewhere herein. The projections may be dissolvable or absorbable to disintegrate after the embedment device has embedded the tissue wall. In some embodiments, the body may also be dissolvable or absorbable. In one embodiment, the body is configured to be removed following embedment of the embedment device.

In some embodiments, an outwardly directed force may be applied by a positioning device to compress the body 12 against a tissue wall to embed the body 12, which may include a structure or other reinforcement material. For example, a positioning device may include an inflatable device, such as a balloon, that may be inflated within the lumen to apply outwardly directed force and thereby compress the body 12 against the tissue wall to embed the body 12 within. In another example, the positioning device may include a pneumatic gas or other fluid filled device. In one example, the positioning device may include a device having an actuator configured to actuate using pneumatic gas or fluid to apply outward directed force. In certain examples, the body 12 includes an embedment structure along a perimeter having a radial dimension with respect to the body that is dimensioned to extend within multiple layers of a tissue wall. The embedment structure may completely embed within the tissue wall. For example, the body 12 may include a wire positioned along a perimeter having a radial dimension that extends into the tissue when compressed there against wherein the wire embeds completely such that the tissue along the tissue wall surrounds the wire. In some examples, the radial dimension may be greater than used with an outwardly biased body 12 to extend a greater distance therein.

In some embodiments, an embedment device 10 may include a plurality of embedment structures that may be embedded by application of outwardly directed force wherein the structures are not connected. For example, an inflatable balloon or other pneumatic or fluid inflatable or actuatable device may temporarily retain a body comprising embedment structures that may be compressed against a tissue wall and then be released when sufficiently embedded. The release may be via release of magnetic attraction, breaking of chemical or adhesive bonds, mechanical, or deformation of the embedment structure or retaining structure, for example. In one embodiment, an embedment device 10 includes a body 12 comprising a wire mesh. The wire mesh may be temporarily retained, e.g., positioned around a perimeter of an inflatable balloon. The balloon may be positioned at a target site and inflated to expand the expandable dimension of the mesh and compress the body against a surrounding tissue wall. When the body embeds the wall, the balloon may be deflated and removed.

In one embodiment, the body 12 of an embedment device 10 includes contact points positioned inwardly with respect to outwardly positioned embedment structures, to engage a positioning device comprising an expansion device. The outwardly directed force applied by the expansion device at the contact points may translate to outwardly directed force along the embedment structures to more fully embed the embedment structures, such as completely. The contact points may include connectors that connect the embedment structures to the contact points. In various embodiments, contact points may partly or completely embed the tissue wall.

In another embodiment, a positioning device includes expanders, ratchets, rails and groove, clamps, or other adjustable couplings. For example, pawl and teeth or gear track may be manipulated to introduce an expanding force. In one example, a clamp may be used to couple portions of the one or more annular structures. The clamp may include a gear, such as a worm gear, that may be manipulated to cause relative sliding between two coupled portions wherein at least one of the portions includes a gear track configured to operably interact with the gear to adjust a diameter or circumference of the positioning device and hence the body 12. The adjustment may be manual, e.g., by manually turning the gear. In some embodiments, the adjustment may be accomplished in situ remotely, external to the lumen, using magnets or electromagnetic fields. In one embodiment, the positioning device includes a motor operatively coupled to a gear and that may be remotely addressable to adjust the circumference or diameter of the positioning device. For example, the positioning device may include a receiver operatively coupled to the motor to receive adjustment signals, such as magnetic or electromagnetic communication signals. The positioning device may also include a controller to control the adjustment operation of the positioning device. In some embodiments, the embedment device 10 is configured to include a positing device. For example, the embedment device 10 may include expanders, ratchets, rails and groove, clamps, or other adjustable couplings. In one example, the embedment device 10 may include projections to engage tissue as described above and elsewhere herein with respect to the positioning device. The projections may be dissolvable or absorbable.

In various embodiments, embedment may be accomplished approximately at the same time the embedment device is delivered to the target region. For example, an anchor device may be anchored to the embedment device within minutes or during the same procedure. In some applications, suitable embedment for anchoring an anchor device may occur in 48 hours or less, 36 hours or less, 24 hours or less, or 12 hours or less. A method of strengthening a portion of a GI tract may include a method of accelerating the embedment process. For example, a positioning device such as an inflatable balloon or cylinder, a rigid structure, sutures, hooks, or pins may be used to compress the embedment device and/or retain the location of the embedment device. In one embodiment, a positioning device may include a plurality of staples or sutures that staple or suture the embedment device into position but do not extend to an exterior side of the tissue wall. The embedment device may include various features configured to assist in embedment and retention. Such features may be configured to decrease the time to sufficiently embed for strengthen or anchoring of an anchor device, for example. Such features may be instead of or in addition to outward directed force, compression, or negative pressure used alone or together with other devices such as positioning devices.

As introduced above (see, e.g., FIGS. 1-3), an embedment device 10 body 12 may include wires 30. The wires may 30 have arcuate, multi-sided, geometric or non-geometric, such as square or rectangular cross-section shapes. FIGS. 24A-24D illustrate example cross-section shapes of wires 30a-30d. The wire 30a shown in FIG. 24A includes a circular or round cross-section shape. The wires 30b, 30d shown in FIGS. 24B & 24D include quadrilateral cross-sections shapes comprising square and rectangular cross-section shapes, respectively. The wire 30c shown in FIG. 24C includes a wedge or triangular cross-section shape. In various embodiments, an embedment device 10 body 12 (see, e.g., FIGS. 1-3) may include wire 30 having a cross-section shape including an edge that is directed outward of the body 12 to assist in penetration of the tissue wall. For example, wire 30c may be orientated such that an edge 31 is directed outward to engage tissue. In some embodiments, projections such as hooks, barbs, or pins may be positioned on one or more sides of a wire 30a-30d to hold or retain the position of the wire when embedding in the tissue wall. As indicated above and elsewhere herein, such projections may be referred to as positioning devices.

As also introduced above, the embedment device 10 may have a body 12 including an embedment structure configured to assist in the embedding process. For example, wires 30 may be dimensioned to assist in tissue penetration such that edges are directed toward tissue. In some embodiments, embedment structures, such as wires 30, may be coated with chemicals to disrupt tissue. For example, embedment structures may be coated with acid. In one embodiment, embedment structures may be heated to assist in penetration of tissue. An electric current or electric pulse may be provided along the embedment structure to heat the structure, provide cautery effect, or otherwise assist in penetrating tissue to embed the embedment structure therein.

Figure 4:
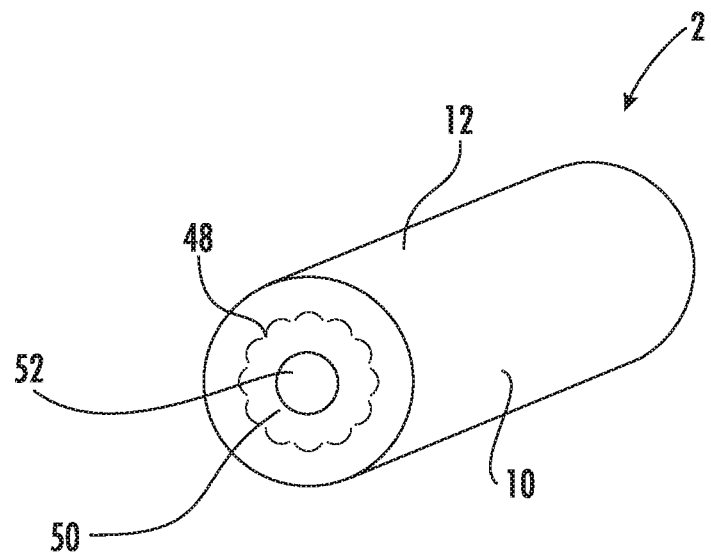
FIG. 4 illustrates an embedment device according to various embodiments described herein.

FIG. 4 illustrates an embodiment of an embedment device wherein the body 12 comprises threaded wire 48. The wire 48 may be threaded into a tissue wall 50 defining a lumen 52. The wire may include a metal, alloy, or polymer wire that may be threaded along a perimeter of a wall defining a lumen. The wire 48 may be threaded to define a generally tubular shape defining a cross-section. According to various embodiments, a method of reinforcing a biological lumen comprises threading a wire 48 along a tissue wall defining the lumen. The wire 48 may be threaded into the tissue wall utilizing endoscopic techniques. Once threaded, the wire 48 may embed the tissue wall 50.

Figure 5:
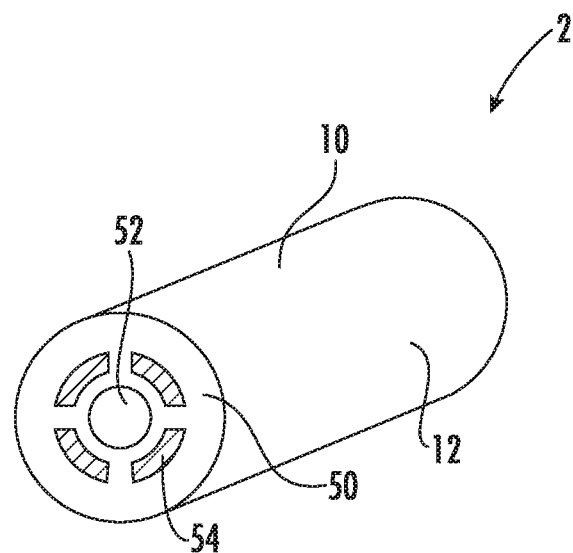
FIG. 5 illustrates an embedment device according to various embodiments described herein.

FIG. 5 illustrates an embodiment of an embedment device 10 wherein the body 12 comprises a polymer composition 54. The polymer composition 54 may be embedded at one or more locations along a tissue wall 50 defining a biological lumen 52. The polymer composition 54 may be injected from a syringe or implanted. The polymer composition 54 may be injected as a liquid or semi-solid. In some examples, the polymer composition 54 may solidify once injected or implanted and therein form an embedded semi-solid or solid. The polymer composition 54 may be embedded at multiple locations along the tissue wall 50. In some instances, the multiple locations or pockets of polymer composition 54 may interconnect. The interconnection may be formed by connecting segments of polymer composition 54. In this or another embodiment, interconnections may be formed by threaded wires, such as threaded wires 48 described with respect to FIG. 4, which may be threaded or implanted between embedded pockets of embedded polymer composition 54. For example, the polymer may be a two part biocompatible polymer. In one embodiment, the embedment device 10 includes a two part biocompatible polymer for injection into the mucosa or submucosa of a tissue wall defining the gastrointestinal tract.

With continued reference to FIGS. 1-8, the embedment device 10 may embed by pushing into the tissue. The embedment may effectively be instantaneous or immediate. The embedment structure of the body 12 may penetrate into the tissue wall.

Embedment of an embedment device 10 may be assisted by holding in place temporarily with projections such as hooks, barbs, or pins. These projections may be referred to as positioning devices or attachment structures (see, e.g., FIG. 6). In some embodiments, an anchor device may be immediately implanted at this time. The hooks or pins may be associated with the embedment device or a separate device, such as a positioning device. For example, a portion of the embedment device 10 or a positioning device may temporarily assist in holding a position of the embedment device and may later be removed when sufficient embedment of the embedment device 10 has be achieved. The embedment device 10 may be sutured into the wall.

In some embodiments, another device such as a positioning device may assist in embedding or retaining the position of an embedment device by compressing the embedment device 10 or embedment structure thereof against the tissue wall. For example, compression may be application of outward directed force, e.g., an inflatable device that may be inflated within the lumen to compress the embedment device against the tissue wall.

Figure 25:
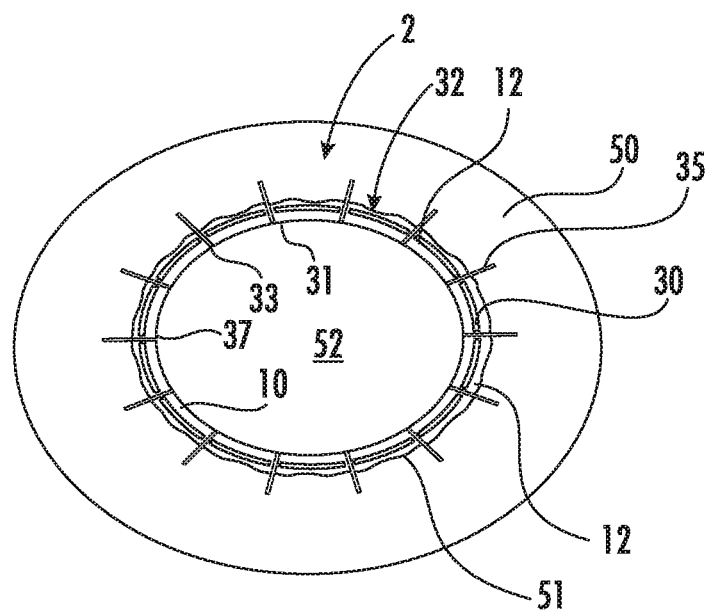
FIG. 25 illustrates a cross-section of a tissue wall wherein a positioning device is assisting the positioning or embedment of an embedment device according to various embodiments.

FIG. 25 illustrates a cross-section of a tissue wall 50 defining a lumen 52 wherein a positioning device 31 assists the positioning or embedment of an embedment device 10 according to various embodiments. The embedment device 10 includes a body 12 defining openings 32. In the illustrated embodiment, the openings 32 are formed by wires 30 or a wire mesh, which may be braided. The wires 30 are positioned against an inner lining 51 of the tissue wall 50.

The positioning device 31 includes a body 33 comprising a plurality of projections 35 extending from outer perimeter 37 of the body 33. The projections 35 may comprise hooks, barbs, or pins, for example. The outer perimeter 37 of the body 33 may include an outer wall or structure such as a wire mesh, cross hatch, matrix, or rails, for example. The outer perimeter 37 may include or expand to a complementary cross-section shape with respect to the body 12 or portion thereof. The body 33 may have a generally tubular cross-section, for example. The projections 35 extend through openings 32 to penetrate the inner lining 51 of the tissue wall 51. In some embodiments, projections 35 include "U" shaped projections, such as staples or staple-like projections, wherein a pair of connected projection 35 penetrate the inner lining 51 and straddle a portion or the embedment device 10 body 12, such as a wire 30. In one embodiment, such projections may be uses without the body 33 to secure the position of the embedment device 10 during embedment. The positioning device 31 may be positioned with the embedment device 10 or separately. For example, the positioning device 31 may be coupled to the embedment device 10 for delivery and may be deployed with the embedment device 10. Both or one of the embedment device 10 and positioning device 31 may be configured to expand or otherwise bias outward. The expansion or bias may result in the projections 35 of the positioning device 31 penetrating the tissue wall 50. In one example, the body 33 of the positioning device 31 comprises an expandable material or an expandable cross-section shape as described herein with respect to the embedment device 10. The body 33 may then assist in embedding the embedment device 10, e.g., by applying outward directed force to compress the embedment device 31 against the inner lining 51 or preventing the embedment device from disengaging the inner lining 51 of the tissue wall 50. The positioning device 31 may be removed when the embedment device 10 has sufficiently embedded the tissue wall 50.

Compression via a positioning device 31 may also be by application of inward directed force or pulling of the inner lining 51 of the tissue wall 50 inward. For example, a suction or negative pressure may be applied locally to open regions between embedment structures to pull tissue positioned in the openings inward.

With further reference to FIGS. 26A-26D, suction or negative pressure may be applied by a positioning device 31. The body 33 of the positioning device 31 may define various openings 39 from which suction or negative pressure may be applied. The positioning device 31 may comprise a tip for a surgical suction or aspirator. For example, the positioning device 31 may couple to a surgical suction or aspirator nozzle.

The positioning device 31 may also be a device that may be positioning in the lumen and initiated to apply suction or negative pressure. For example, the body 33 may define an inner volume that fluidically couples with openings 39. The body 33 may be positioned in the lumen 52 and a suction may be applied, e.g., by actuating a plunger fluidically coupled to the interior volume or application of suction at a suction opening/hole or valve, which may be a one way value or a valve that may be modified to prevent fluid flow in one or more both directions. Once suction or negative pressure has been applied at the openings to tissue, the inner volume may otherwise be sealed or capped, which may be performed by operation of a one-way valve.

Figure 26A:
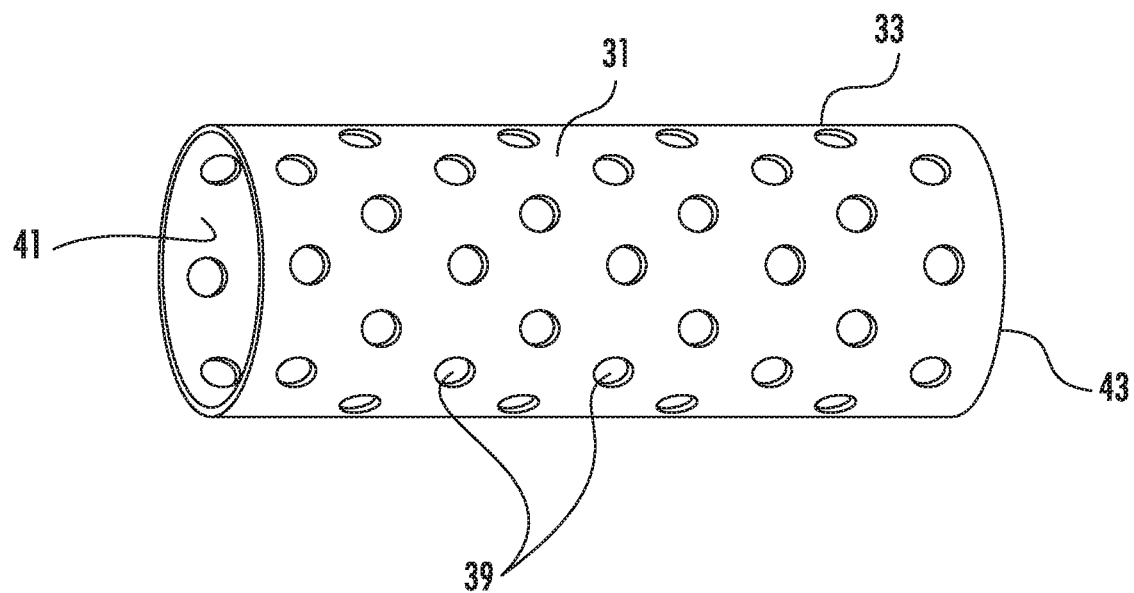
FIGS. 26A-26D illustrates positioning devices for assisting in the positioning or embedment of an embedment device according to various embodiments.

The positioning device 31 illustrated in FIG. 26A includes a generally tubular body 31 defining a plurality of openings 39. The openings 39 may be positioned to correspond to opening 32 locations defined by an embedment device 10 (see, e.g., FIG. 1). The positioning device 31 may be configured for use as surgical suction tip. In another application, the positioning device 31 may be configured for use as a separate device for temporarily leaving in the lumen. For example, the body 33 may include a distal wall 43 that encloses an inner volume 41 at a distal end of the body 33. Suction or negative pressure may be applied proximally within the lumen to pull tissue into openings 39. Suction or negative pressure may be applied by surgical suction, actuation of a plunger (not shown) within the inner volume 41, for example. The body 31 may be sufficiently rigid to avoid collapsing upon application of suction or negative pressure. In some embodiments, a proximal end of the body 31 may be capped or sealed to maintain the interior pressure. For example, the embodiment illustrated in FIG. 26D is similar to FIG. 26A and includes a valve 47 at the proximal end enclosing the inner volume 41 at the proximal end of the body 33. The valve may be a one way valve or a two way valve. For example, the valve 47 is a two way valve that may be initiated to maintain or release a vacuum pressure. In another example, the valve 47 is a one way valve from which vacuum pressure may be established. In one embodiment, the valve includes a plunger than may be actuated in a first direction to create vacuum pressure and actuated in a second direction to increase pressure. The body 33 may also include a vacuum release valve (not shown), e.g., along the proximal end wall.

Figure 26B:
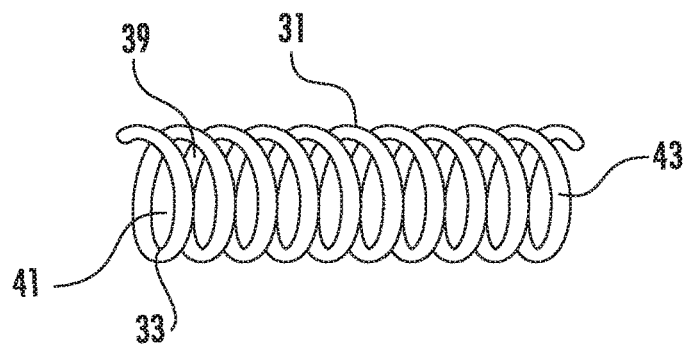

The positioning device illustrated in FIG. 26B includes a generally tubular body 31 defining a plurality of openings 39. The openings 39 may be positioned to correspond to opening 32 locations defined by an embedment device 10 (see, e.g., FIG. 2). The positioning device 31 may be configured for use as surgical suction tip. In another application, the positioning device 31 may be configured for use as a separate device for temporarily leaving in the lumen. For example, the body 33 may include a distal wall 43 that encloses an inner volume 41 at a distal end of the body 33. Suction or negative pressure may be applied proximally within the lumen to pull tissue into openings 39. Suction or negative pressure may be applied by surgical suction, actuation of a plunger (not shown) within the inner volume 41, for example. The body 31 may be sufficiently rigid to avoid collapsing upon application of suction or negative pressure. In some embodiments, a proximal end of the body 31 may be capped or sealed to maintain the interior pressure, for example, as described above with respect to FIG. 26D. A valve, plunger, or both may also be included.

Figure 26C:
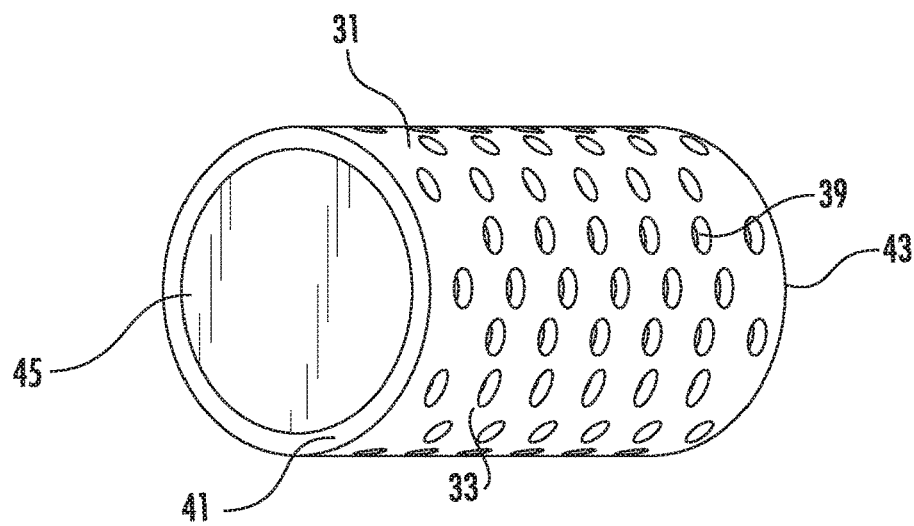
Figure 26D:
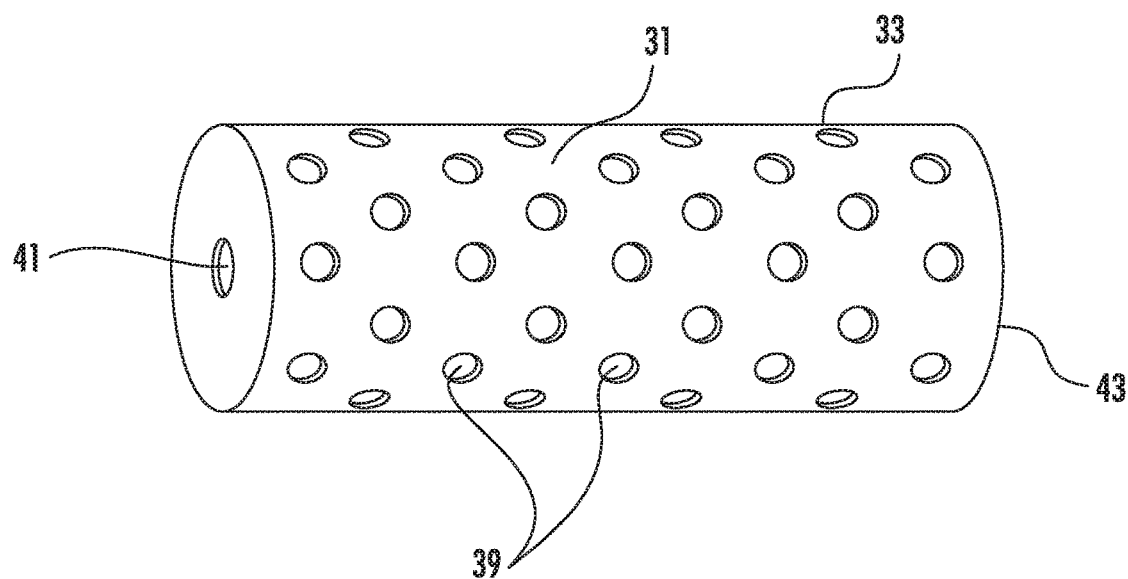

The positioning device illustrated in FIG. 26C includes a generally tubular body 31 defining a plurality of openings 39 along an outer perimeter. The openings 39 may be positioned to correspond to opening 32 locations defined by an embedment device 10 (see, e.g., FIG. 1). The body 31 also includes an inner wall 45 defining a portion of the inner volume 41. The positioning device 31 may be configured for use as surgical suction tip. In another application, the positioning device 31 may be configured for use as a separate device for temporarily leaving in the lumen. For example, the body 33 may include a distal wall 43 that encloses an inner volume 41 at a distal end of the body 33. Suction or negative pressure may be applied proximally within the lumen to pull tissue into openings 39. Suction or negative pressure may be applied by surgical suction, actuation of a plunger (not shown) within the inner volume 41, for example. The body 31 may be sufficiently rigid to avoid collapsing upon application of suction or negative pressure. In some embodiments, a proximal end of the body 31 may be capped or sealed to maintain the interior pressure, for example, as described above with respect to FIG. 26D. A valve, plunger, or both may also be included. In this embodiment, the positioning device 31 defined a hollow central path through which material may pass while the positioning device 31 is positioned within the lumen 52 (see FIG. 25).

With continued reference to FIGS. 25-26D projections 35 may be removed or vacuum may be released when the embedment device has embedded the tissue wall 50. The positioning device 31 may then be withdrawn from the lumen 52. As also noted above, the body 33 may be sufficiently rigid to maintain the suction or negative pressure. In some embodiments, the body 33 may also compress the embedment device 10 against the tissue wall. The body 33 may be collapsible for later removal when the embedment structure of the embedment device 10 has sufficiently embedded. For example, the body 33 may be mechanically collapsible, e.g., with hinges or slidable sections. In another example, the body 33 may be collapsible by modification of the body 33, e.g., a shape change or shape memory material that may be triggered to collapse or obtain a collapsible conformation. In another embodiment, the positioning device 31 may be removed without collapsing the body 33.

With continued reference to FIGS. 1-8, in various embodiments, an embedment device 10 may be configured to prevent degree or depth of migration of the body 12 with respect to the tissue wall of a lumen. For example, the embedment device 10 may be configured such that an embedded portion of the body 12 does not migrate completely through the tissue wall of the lumen.

An embedment device 10 may include an embedding conformation in which outward force, extension, or both is limited in time, distance, or both. For example, in the embedding conformation, the body 12 may apply outward force against the tissue wall until a circumference or perimeter of the body 12 has reached a predetermined length or achieved a predetermined cross-section shape or dimension therein to obtain the embedded conformation. In another example, outward force may be applied by a larger dimension of the body 12 that expands the corresponding dimension of the lumen. The body 12 may embed the lumen such that the embedded structure does not continue to apply outward force and the corresponding dimension of the lumen decreases to a dimension less than the greater dimension of the body 12. The tissue defining the lumen may cover the body 12 or embedded portions thereof in the embedded conformation. In some embodiments, the embedment device 10 limits migration by embedding in the tissue walls wherein the tissue lodging is used as support from potential migration.

Figure 27:
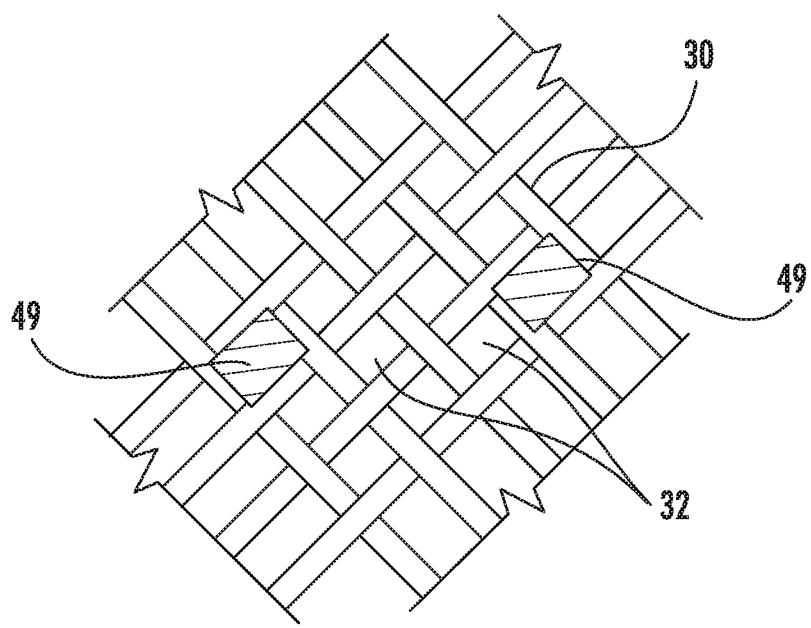
FIG. 27 illustrates an embedment device configured to prevent migration of the device through a tissue wall according to various embodiments.

FIG. 27 illustrates a magnified view of a body 12 configuration of an embedment device (e.g., any of the embedment devices 10 described with respect to FIGS. 1-8 & 25) comprising a physical block 49 to migration. For example, the body 12 includes wires 30 defining openings 32. Positioned between the openings is a physical block 49 to migration comprising a material of film that covers one or more openings. The physical block 49 provides a material expanse between adjacent openings 32 that prevents the block 49 portion from embedding in a tissue wall or otherwise inhibits migration through the wall. The block 49 may include various dimensions, such as ⅛ inch or more, ¼ inch or more, ½ inch or more, ¾ inch or more, or 1 inch or more, for example. The number and proximity of blocks 49 may vary. For example, blocks 49 may be arranged at spaced intervals of a couple inches or more. In one example, a block 49 is positioned at a distal portion, a central portion, and a proximal portion of the body.

As introduce above, in various embodiments, the embedment device 10 may be configured to prevent a tissue wall defining a lumen from expanding away from a force applied to the wall, which may be outward, e.g., pushing, or inward directed, e.g., pulling, forces. For example, the body 12 may provide an embedded scaffold that limits expansion or contraction of the wall to pushing or pulling forces. The body 12 of the embedment device 10 may have a maximum cross-section dimension or perimeter dimension, e.g., circumference. In some embodiments, the body 12 of the embedment 10 device may lack rigidity in shape such that the lumen may contract inwardly when the embedment structure in embedded. However, in one embodiment, the body 12 of the embedment device 10 may be rigid at one or more portions to limit inward contractions. In some examples, the body 12 in the embedding or embedded conformation defines a rigid circumference, perimeter, cross-section shape, diameter or other dimension. In these or other examples, the body 12 in the embedding or embedded conformation defines a maximum circumference, perimeter, or diameter having little to no practical range of increase. In various embodiments, the maximum circumference, perimeter, diameter or other dimension may be rigid or flexible in cross-section. In one embodiment, one or portions of the circumference, perimeter, diameter or other dimension are rigid while one or more other portions are flexible. In some examples, portions may have differential rigidity and flexibility. For example, a body 12 comprising threaded flexible string or mesh may allow approximately native flexibility with respect to the cross-section of the lumen but may limit the maximum circumference or perimeter the tissue wall may achieve.

In one embodiment, an embedment device 10 for reinforcement of the gastrointestinal tract may include a body 12 dimensioned to limit expansion to a cross-section dimension that is less than a cross-section dimension, such as a maximum cross-section dimension, defined by the adventitia, which forms the outermost layer of the gastrointestinal tract. The body 12 may include an enlarged maximum cross-section dimension that corresponds to the cross-section dimension in the embedding and embedded conformations or may include an embedding conformation wherein the cross-section dimension is less than the maximum cross-section dimension and the body 12 is biased to expand to the maximum cross-section dimension to transition to the embedded conformation.

Figure 6:
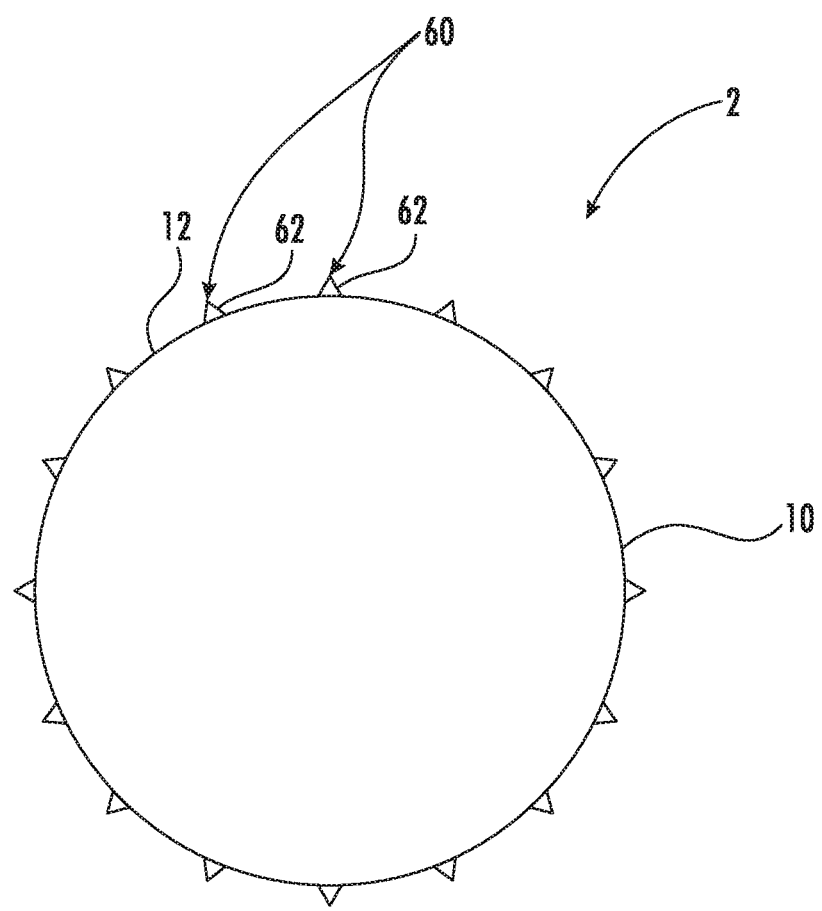
FIG. 6 illustrates an embedment device according to various embodiments described herein.

FIG. 6 provides an end view of an embedment device 10 according to various embodiments. The embedment device 10 includes one or more attachment structures 60 comprising projections 62 that extend outwardly about a perimeter of the body 12. In various embodiments, attachment structures 60 may be referred to as positioning devices attached to the embedment device 10 or body 12 thereof. For example, attachment structures 60 may be configured to assist in initial attachment or stability of the embedment device 10 at the target site. In one example, attachment structures 60 may include projections 62 configured to penetrate tissue along a wall defining a lumen. Projections 62 may include barbs, hooks, or straight projections such as pins, for example. Additionally or alternatively, attachment structures 60 may include sutures (not shown). For example, a body 12 of an embedment device 10 may be sutured or sewn to a tissue wall.

In some examples, the attachment structures 60 may be absorbable such as absorbable projections, absorbable barbs, absorbable sutures, or absorbable hooks. Attachment structures 60 may be positioned at one or more locations along the body 12. For example, one or more rows of barbs or hooks may be positioned along a length or about a perimeter of the body 12. In various embodiments, attachment structures 60 are dimensioned to not extend completely through the tissue wall defining the lumen. For example, a length of the attachment structures 60 may be limited to less than a thickness of a tissue wall as to not puncture through the wall.

Attachment structures 60 may assist in positioning of the embedment device 10 at the target site prior to embedment. The embedment device 10 or body 12 may subsequently at least partially embed the tissue wall to reinforce and strengthen the wall. In some embodiments, an embedment device 10 may be attached at a target site via attachment structures 60 and an anchor device may be anchored to the target site in a single procedure. In other embodiments, an embedment device may be attached at a target site via attachment structures 60 and an anchor device may be anchored to the target site in a subsequent procedure. The subsequent procedure may take place the next day or sometime thereafter. In some instances, the subsequent procedure may take place after the embedment device 10 has at least partially or completely embedded the tissue.

Embodiments of the embedment device 10 may embed and therein reinforce a tissue wall of the gastrointestinal tract. For example, the gastrointestinal tract generally contains four tissue layers. Starting from the innermost layer and moving outward, the gastrointestinal tract includes the following layers: mucosa, submucosa, muscularis propria, and the adventitia or serosa, which is the outermost layer. In various embodiments, the embedment device may embed within the mucosa, such as within the lamina propria, muscularis mucosa, or both. In further embodiments, the embedment device embeds within the submucosa. The embedment device may embed completely within the mucosa, submucosa, or extend within both. In one embodiment, the embedment device 10 or portion thereof may extend to or within the muscularis propria.

In various embodiments, the embedment devices 10 described herein, including those illustrated in FIGS. 1-5, 7 & 8, may include attachment structures 60 or positioning devices along a perimeter of the body 12.

In various embodiments, an embedment device 10 includes a body 12 comprising a double wall configuration or a configuration having an outer portion positioned to compress against and embed a tissue wall defining a biological lumen. The body 12 may further include an inner positioned portion attached to the outer positioned portion configured to provide a scaffold or coupling platform onto which another device may couple to anchor within the lumen.

Figure 7:
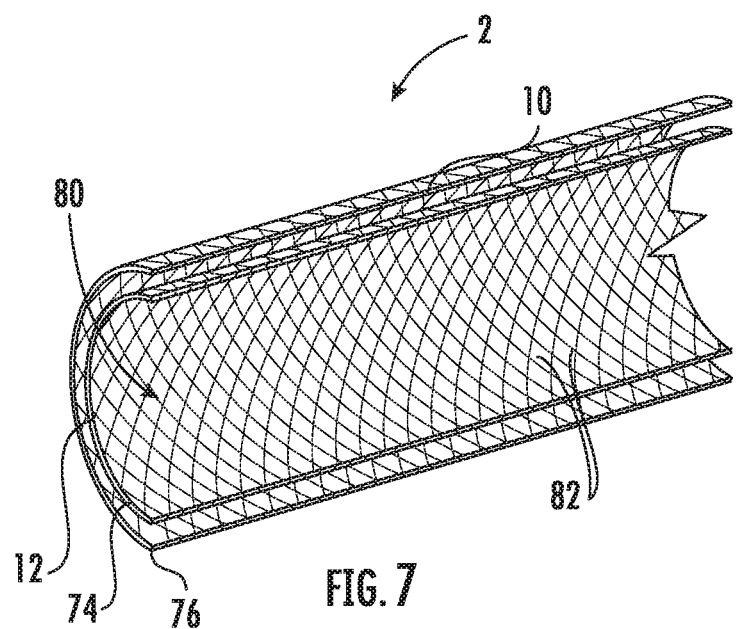
FIG. 7 illustrates a cross-section of an embedment device according to various embodiments described herein.

FIG. 7 illustrates an example of an embedment device 10 having a body 12 comprising an outer portion 76 configured to embed a tissue wall and an inner portion 74 comprising a coupling platform 80. The body 12 includes a multi-layer mesh configuration wherein the outer portion 76 comprises an outer layer configured to embed a tissue wall and the inner portion 74 comprises an inner layer. The inner layer may be configured to remain at least partially unembedded in use.

The outer portion 76 may include an embedment structure configuration consistent with the present disclosure to embed the tissue wall. For example, the outer portion 76 may include threaded wire, coil, injected polymer, or combinations thereof. In the illustrated embodiment, the outer portion 76 comprises a mesh structure similar to that described with respect to FIG. 1.

The outer portion 74 may include an embedment structure configuration consistent with the present disclosure to embed the tissue wall. For example, the outer portion 74 may include threaded wire, coil, injected polymer, or combinations thereof. In the illustrated embodiment, the outer portion 74 comprises a mesh structure similar to that described with respect to FIG. 1.

The coupling platform 80 provides a platform onto which another device, such as an anchor device, which may or may not include a medical device, may couple. For example, the coupling platform 80 includes one or more couplings 82 configured to couple to one or more corresponding couplings of another coupling platform. A coupling 82 may refer to mating surfaces, structures having male and female relationships as well as adhesive or attractive surfaces, suction, sliding, compression fit, interlocking relationships, and combinations thereof. Couplings 82 may comprise one or more of openings, slots, grooves, rails, latches, flanges, rims magnets, projections, lips, sockets, pins, clips, hooks, loops, or ball and socket configurations, for example. Any of which may comprise a coupling surface. In various embodiments, a coupling surface may include interlocking or touch fasteners, e.g., hook-and-loop, suction or micro-suction structures, adhesives, magnets, or other coupling structures in which to couple a corresponding coupling. As shown, the one or more couplings 82 include rails and openings. Corresponding couplings such as latches, projections, e.g., hooks, may couple to the rails or within openings. As noted above, the rails may include coupling surfaces incorporating interlocking or touch fasteners, adhesives, magnets, or magnet attractive material.

The outer portion 76 may be configured to apply outwardly directed force along the tissue wall to embed therein as described above and elsewhere herein. In further embodiments, the outer portion 76 may include multiple layers of mesh configured to embed the tissue wall.

The inner and outer portions 74, 76 may be coupled by one or more connectors (not visible). The one or more connectors may be dimensioned to provide a suitable distance between the outer portion 76 and the coupling platform 80 of the inner portion 74. The one or more connectors may also be dimensioned to provide a suitable distance between the coupling platform 80 and tissue wall when the outer portion 76 embeds the wall. For example, the one or more connectors may prevent the coupling platform 80 from embedding within the tissue wall, which may include not completely embedding within the tissue wall. The one or more connectors may comprise wires extending between the outer portion 76 and the inner portion 74. The one or more connectors may be may be rigid or flexible. In one example, a connector includes threaded wire. In another example, the inner portion 74 and outer portion 76 may fold into each other at one or both ends of the body 12.

In some configurations, the coupling platform 80 or connector includes a cover or shroud that extends between a perimeter of the outer portion 76 and the inner portion 74. Such an embodiment may find beneficial application when it is desired to limit or prevent passage through the lumen between the coupling platform 80 and the outer portion 76 or tissue wall. In one embodiment, the outer portion 76 includes a cover or shroud. Similarly, the anchor system 2 may include an anchor device having a lip or flange about a perimeter to limit or prevent passage of material along the perimeter of the lumen.

Figure 8:
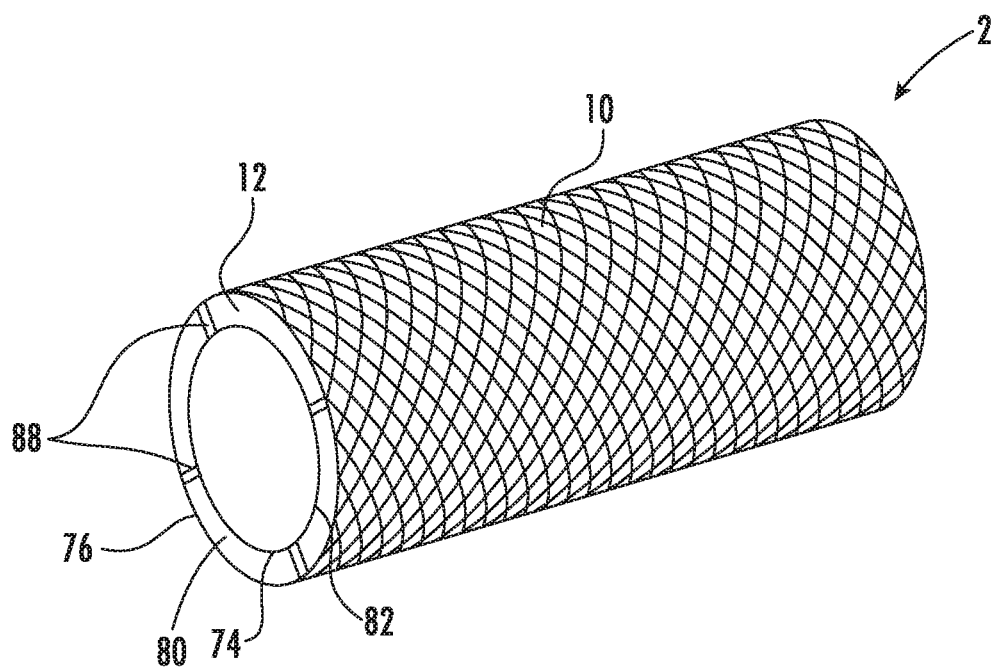
FIG. 8 illustrates an embedment device according to various embodiments described herein.

FIG. 8 illustrates an embodiment of an embedment device 10 having a generally tubular body 12 comprising an outer portion 76 configured to embed a tissue wall and an inner portion 74 comprising a coupling platform 80. The outer portion 76 may include an embedment structure configuration consistent with the present disclosure to embed the tissue wall. For example, the outer portion 76 may include threaded wire, coil, injected polymer, or combinations thereof. In the illustrated embodiment, the outer portion 76 includes a wire mesh forming an outer perimeter of the body 12 and is configured to apply outwardly directed force against a tissue wall defining a lumen in a manner similar to that described with respect to FIG. 1.

The coupling platform 80 includes one or more couplings 82 comprising a rail. The rail extends around an inner perimeter and forms a ring configured to position within the lumen, inward of the tissue wall, when the outer portion 76 embeds the tissue wall. The coupling platform 80 provides a platform onto which another device having a coupling platform comprising one or more corresponding couplings may couple. For example, an anchor device, which may or may not include a medical device, comprising a coupling platform having one or more couplings comprising latches or projections, e.g., hooks, may couple to the rail. Other coupling arrangements may be used, such as any of those described herein. For example, the coupling platform 80 may include a coupling 82 incorporating magnets, hook-and-loop, suction or micro-suction structures, or adhesive configured to assist in coupling to a corresponding coupling. In some examples, such couplings 82 include coupling surfaces incorporating magnets, hook-and-loop, suction or micro-suction structures, adhesives, or magnet attractive materials. In another example, one or more additional rails may be included to increase coupling points or to provide flexibility in coupling location. Additional rails may further form one or more additional couplings 82 such as openings, gaps, slots, or grooves into which corresponding couplings such as pins, clips, lips, rails or combinations thereof may couple. Other configurations may also be used such as ball and socket couplings. In any of the coupling configurations, magnets or magnet attractive materials may be used, such as incorporated with one or more particular coupling structures or separately.

One or more connectors 88 couple the outer portion 76 and the coupling platform 80. The one or more connectors 88 may be dimensioned to provide a suitable distance between the outer portion 76 and the coupling platform 80 of the inner portion 74 such that the coupling platform 80 does not completely embed the tissue wall, which may include not contacting the tissue wall. The one or more connectors 88 may comprise wires, which may be rigid or flexible. In one example, the connectors 88 comprise threaded wire. In some configurations, the body 12 may include a cover or shroud as described above with respect to FIG. 7.

With reference again to FIG. 23, the anchoring system 2 may include a delivery device 20 configured to deliver the embedment device 10. For example, the embedment device 10 may be delivered utilizing a delivery device 20 employing a minimally invasive technique such as keyhole surgery, e.g., endoscopic or laparoscopic, through a natural body orifice, such as the mouth, anus, ear canal, nose, or vagina, natural orifice transluminal endoscopic surgery, or other suitable procedure. In one example, delivery of the embedment device 10 to the esophagus 136 may include passing a delivery device tube or sheath 22 through the mouth and into the esophagus 136. In further embodiments, the embedment device 10 may be delivered into the stomach 138 or through the stomach 138 and into the duodenum 140.

The delivery device 10 may include a proximal end 68 for directing and manipulating a rigid or flexible sheath 22 having a distal end 70 for coupling to and/or manipulating the embedment device 10. In some embodiments, the distal end 70 may include a retainer 29 to retain the embedment device 10 in a delivery conformation. The delivery device 20 may be configured to allow release of the embedment device 10 at the target site 24. Release of the embedment device 10 may include actuating the delivery device 10 to release a clamp, grasper, or expel the embedment device 10 from distal pocket or a distal end 70 of the delivery sheath 22, for example. In the illustrated embodiment, a plunger 28 may be used to urge the embedment device 10 from the distal end 70 of the sheath 22. In some embodiments, release of the embedment device 10 at the target site 24 may accompany release of a retainer to allow the embedment device 10 to transition to an embedding conformation. For example, release may include removal of the embedment device 10 from a restricted volume, such as expelling the embedment device 10 from an opening in a tube or pocket within the sheath 22, the release of a clamp, removal of one or more pins, relatively sliding a brace or bracket and the embedment device 10 to remove the coupling, or combinations thereof. In some embodiments, a separate device may be used to release the retainer. In some embodiments, the embedment device 10 stably maintains a delivery conformation without utilization of a retainer that may be associated with the delivery device or a separate retainer. For example, the embedment device 10 may comprise a shape change or shape memory material configured to change shape or obtain a memory shape comprising an embedding or embedded conformation. In one embodiment, the delivery device does not include a retainer.

The delivery device 20 or a separate device may assist in transitioning the embedment device 10 from the delivery conformation to the embedding conformation. For example, as introduced above, the delivery device 20 may release the embedment device 10 from a restrictive volume or release a retainer, reducing conformational stresses to allow the embedment device 10 to transition to the embedding conformation and apply outwardly directed force along one or more portions of the tissue wall. In some embodiments, the embedding conformation corresponds to the embedding conformation such that the transition from the delivery conformation to the embedding conformation results in the embedment device obtaining its maximum embedded dimension. Embedment devices 10 including shape change or shape memory materials may be selected to respond to various environmental conditions such as temperature. The delivery device 20 or a separate device may be configured to establish an environmental condition, e.g., induce an electromagnetic field, impart an electrical current, or generate an electromagnetic field, to support transition to the embedding or embedded conformation.

The delivery device 20 or a separate device may assist in initial positioning or attachment of the embedment device 10. For example, with respect to attachment structures 60 comprising sutures, a delivery device 20 or another device may be used to apply the sutures.

In various embodiments, a delivery device (not shown) includes a syringe, which may include a plurality of syringes. The syringes may be used to inject polymer.

With reference to FIGS. 9-14, and as introduced above, an anchoring system 2 may include an anchor device 90 configured to stably anchor within the lumen. While not illustrated in FIGS. 9-14, anchor devices 90 may include medical devices. For example, a medical device may be integrated with an anchor device 90 to anchor within a lumen. In various embodiments, an anchor device 90 is configured to couple one or more medical devices. In some examples, coupled anchor and medical devices may be delivered to the target site together. In further examples, the anchor device 90 may provide a convenient platform onto which one or more medical devices may be implanted, removed, or both in situ.

An anchor device 90 may include a body 92. The body 92 may comprise one or more annular rings, mesh, helical coil, straight or curved wire, for example. The body 92 may be constructed of metals, alloys, polymers, ceramics, or other suitable materials for locating within a biological lumen. In various embodiments, an anchor device 90 comprises a body 12 having a rigid shape. In one embodiment, the anchor device comprises a body 12 having a flexible shape. In this or another embodiment, the body 12 comprises a shape that is elastic, resilient, or both. The body 12 may include a delivery conformation wherein the body 12 is reduced in at least one dimension relative to an anchor conformation. The delivery conformation may arise from compression or deformation of the body 12 relative to the anchor conformation in a manner similar to that described herein with respect to the embedment device. For example, the anchor device 90 may be retained by a retainer during delivery or may be deformed for delivery and then released to decompress or induced to reform into the anchor conformation when delivered to the target site.

An anchor device 90 may include one or more anchors 96 structured to anchor to the tissue wall. Anchors 96 may comprise projections extending or extendable from the body 92 positioned to engage the tissue wall. In application, anchors 96 may engage a tissue wall having an embedment device embedded or embedding therein. The anchors 96 may typically engage or penetrate the tissue wall to anchor the anchor device 90. In various embodiments, anchors 96 are dimensioned to penetrate tissue walls but not to puncture completely through the wall and thereby traverse the wall to an external side thereof. In some embodiments, the anchor conformation may apply outwardly directed force on the tissue wall of the lumen to assist in engagement of anchors 96.

An anchor 96 may be structured to engage tissue when the anchor device 90 is oriented such that the projections are positioned along an outer portion of the body 92, adjacent to the tissue wall. For example, projections, together or independently may include outwardly directed edges, such as points, to penetrate tissue. The outwardly directed edges may include edges positioned at angles having radial, distal, or proximal components. For example, distally directed edges may be positioned to engage tissue when the anchor device 90 is moved distally. Proximally directed edges may be positioned to engage tissue when the anchor device 90 is moved proximally, while radially directed edges may be positioned to engage tissue when the anchor device 90 is move in a radial direction, which may include radial directions having proximal or distal components. In some examples, projections are structured to hinder ease of extraction from tissue. For example, projections may include proximal extensions, distal extensions, or lateral extensions that extend within tissue and therein hinder extraction of the projection. In some embodiments, projections may include hooks having bends structured to hook tissue within the hook throat. In some embodiments, projections may include barbs, which may be positioned adjacent to projection edges. In some embodiments, a hook may include a barb, which may be located adjacent to an edge, along a bend, or along a shank of the hook.

As introduced above, anchor devices 90 may be configured to anchor to tissue walls embedded with an embedment device. The embedment device may allow for stronger forces to be applied than the native structure could resist. For examples, anchors 96 that penetrate tissue may be prevented from proximal, distal, or circumferential tearing along the tissue wall by an embedded device. The embedded device may provide improved distribution of tearing force along the tissue in which it embeds. For example, in addition to or alternatively to anchors 96 that penetrate tissue, such as hooks, barbs, and straight projections, anchor devices 90 may anchor to a reinforced lumen via direct pressure on the tissue wall. That is, the embedment device may prevent or limit the ability of the tissue walls along the reinforced portion of the lumen to expand away from the direct, outward, pressure. Direct pressure may be provided in a manner similar to that described herein with respect to the embedment device. For example an expandable mesh or coil may be used, which may primarily hook onto the body of the embedded device. Limiting the ability of the lumen to expand may also limit radial tearing from hooks or undesired extraction of straight projections due to excessive lumen expansion. Anchors 96 may also include magnets providing magnetic attraction to the embedment device or may include magnetic attractive materials configured to attract to magnet portions of an embedded device. Attachment with anchors 96 including magnetic attraction with an embedded device may include anchors that penetrate tissue walls or that compress against but do not penetrate tissue walls or interact mechanically or geometrically with the embedded structure. In one example, an anchor device comprises expandable tubing configured to expand to apply direct pressure on the reinforced tissue wall to thereby anchor therein. The expandable tubing may be biased to expand or may include magnetic attraction with an embedment device that expands the tubing to the approximate dimensions of the lumen.

The anchor device 90 illustrated in FIG. 9 includes a body 92. The body 92 is formed or formable into an annular cross-section. The body 92 may comprise metal, alloy, polymer, fabric, ceramic, or combinations thereof, for example. The body 92 may be rigid, flexible, elastic, or resiliently elastic. In some embodiments, the body 92 may comprise a shape change or shape memory material such as nitinol. One or more anchors 96 comprising are located along a perimeter of the body 92 and are positioned or positionable outwardly to engage tissue of a lumen wall. The anchors 96 include hooks to hook tissue. Other anchor configurations such as straight projections or barbs may also be used. The hooks are positioned between an upper rim 98 and a lower rim 99. In a further or another embodiment, the body 92 includes one or more anchors 96 comprising magnets or magnet attractive materials that may or may not penetrate, e.g., puncture, into tissue.

The anchor device 90 illustrated in FIG. 10 includes a body 92 comprising a mesh structure. The mesh structure may be similar to that described above with respect to FIG. 1. The body 96 is formed or formable into an annular cross-section. The body 92 may comprise metal, alloy, polymer, fabric, ceramic, or combinations thereof, for example. The body 92 may be rigid, flexible, elastic, or resiliently elastic. In some embodiments, the body 92 comprises a shape change or shape memory material such as nitinol. In one embodiment, one or both of an upper rim 98 or lower rim 99, corresponding to proximal and distal rims in use, may comprise a rigid or resiliently elastic conformation in use while a central portion of the body 92 comprises a flexible material. In another embodiment, the central portion of the body 92 may comprise a rigid material in use. One or more anchors 96 are located along a perimeter of the body 92 and are positioned or positionable outwardly to engage tissue of a lumen wall or the embedded structure, which may include embedded structures that are embedded materials such as injected polymer. The anchors 96 include hooks to hook tissue or the embedded structure. Other anchor configurations may be used. As illustrated, the body 92 includes hooks positioned along the upper rim 98 and lower rim 99. In a further or another embodiment, the body 92 includes one or more anchors 96 comprising magnets or magnet attractive materials that may or may penetrate, e.g., puncture, into tissue.

The anchor device 90 illustrated in FIG. 11 includes a body 92 formed or formable into an annular cross-section. The body 92 may comprise metal, alloy, polymer, fabric, ceramic, or combinations thereof, for example. The body 92 may be rigid, flexible, elastic, or resiliently elastic. In some embodiments, the body 92 may comprise a shape change or shape memory material such as nitinol. One or more anchors 96 are located along a perimeter of the body 92 and are positioned or positionable outwardly to engage tissue of a lumen wall. The anchors 96 include hooks configured to hook tissue. Other anchor configurations such as barbs or straight projections may be used. In a further or another embodiment, the body 92 includes one or more anchors 96 comprising magnets or magnet attractive materials that may or may not penetrate, e.g., puncture, into tissue.

The anchor device 90 illustrated in FIG. 12 comprises a body 92 formed or formable into an annular cross-section and extending along in a wave pattern. The body 92 may comprise metal, alloy, polymer, fabric, ceramic, or combinations thereof, for example. The body 92 may be rigid, flexible, elastic, or resiliently elastic. In some embodiments, the body 92 may comprise a shape change or shape memory material such as nitinol. One or more anchors 96 are located along a perimeter of the body 92 and are positioned or positionable outwardly to engage tissue of a lumen wall. The anchors 96 include hooks configured to hook tissue. Other anchor configurations such as barbs or straight projections may be used. In a further or another embodiment, the body 92 includes one or more anchors 96 comprising magnets or magnet attractive materials that may or may not penetrate, e.g., puncture, into tissue.

Figure 13:
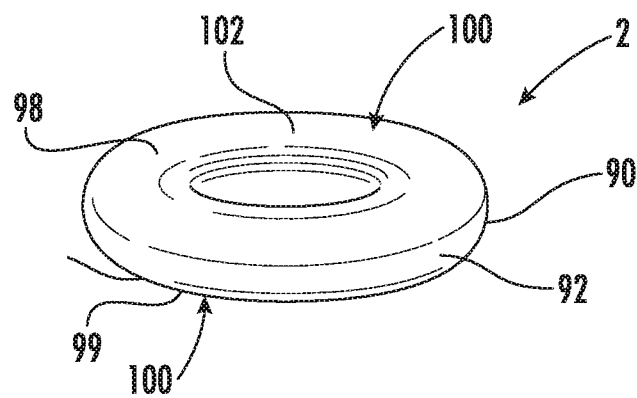
FIG. 13 illustrates an anchor device according to various embodiments described herein.

The anchor device 90 illustrated in FIG. 13 includes a body 96 comprising an inflatable balloon. The body 92 has an annular shape defining a central hole similar to a doughnut. The balloon may be inflated at a target site to compress against a tissue wall. The illustrated anchor device 90 may anchor by application of outwardly directed pressure and does not include anchors, however, in some embodiments, anchors as described herein may be used, e.g., located along a perimeter of the body 92.

As introduced above with respect to FIGS. 7 & 8, in some embodiments, an anchor device 90 may include one or more coupling platforms 100 configured to couple to another coupling platform, such as a coupling platform associated with another anchor device fitted with a medical device. The coupling platform 100 may be similar to the coupling platform and variations thereof described above with respect to FIGS. 7 & 8 and elsewhere herein. The anchor device 90 may include one or more couplings 102 comprising openings, slots, grooves, rails, latches, magnets, coupling surfaces, lips, ball, sockets, pins, clips, hooks, balls, or combinations thereof. For example, the anchor device 90 may include a coupling platform 100 having a coupling 102 comprising a coupling 102 surface configured to couple to a corresponding coupling, which may include a coupling surface, of another anchor device, such as a ledge, lip, or flange. In some embodiments, the coupling 102 may include a textured surface, magnets, or adhesive as described herein. The surface may include structures configured to interlock or touch fasteners, e.g., hook-and-loop, suction or microsuction structures, adhesives, magnets, or other coupling structures in which to couple a corresponding coupling.

As an example, the anchor device 90 illustrated in FIG. 9 may include a coupling platform 100 comprising a coupling 102 along a surface of an upper 98 or lower 99 rim of the body 92. The surface may include a textured surface, magnets, magnet attractive material, interlocking, touch fasteners, or adhesive, as described above and elsewhere herein.

With reference again to the anchor device 90 illustrated in FIG. 10, the body 92 may include a coupling platform 100 comprising one or more couplings 102. For example, one or more couplings 102 comprising rails or wires of the mesh may provide surfaces onto which a corresponding coupling such as a hook, clip, or latch may couple. Couplings 102 may also include openings between the rails or wires into which corresponding couplings such as projections, pins, or clips may couple. In the illustrated embodiment, a diameter of a region of the body between the upper and lower rims 98, 99 is reduced providing a more accessible coupling 102 to which a corresponding coupling may attach. In this or other embodiments, the coupling 102 may incorporate magnets, magnet attractive material, interlocking fastener structures such as touch fasteners, or other coupling configurations described herein.

The embodiments illustrated in FIGS. 11 & 12 may also include a coupling platform 100 comprising a coupling 102 including a rail or wire onto which a corresponding coupling such as a hook, clip, or latch may couple. In these or other embodiments, the coupling 102 may incorporate magnets, magnet attractive material, interlocking fastener structures such as touch fasteners, or other coupling configurations described herein.

As another example, the balloon illustrated in FIG. 13 may also include a coupling platform 100 comprising a coupling 102. For example, the coupling 102 may include a surface defined along an upper or lower rim 98, 99 of the body 92. The surface may couple to a corresponding surface utilizing adhesive, magnets, magnet attractive material, interlocking fastener structures such as touch fasteners. The balloon may also be configured with another coupling as described above with respect to FIGS. 9-12.

Figure 14:
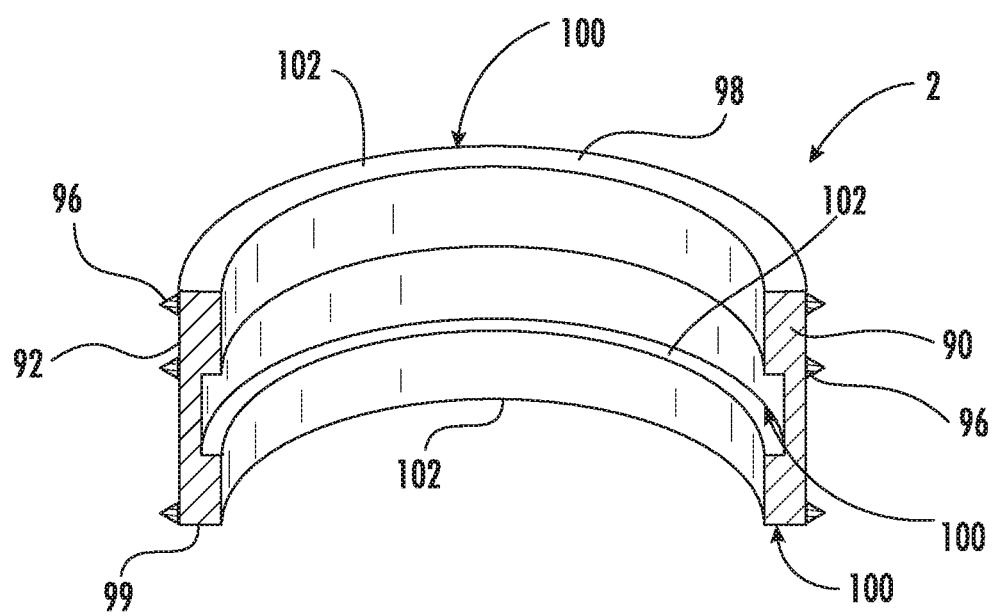
FIG. 14 illustrates a cross-section of an anchor device according to various embodiments described herein.

Another embodiment of an anchor device 90 similar to FIG. 9 including another coupling platform 100 is illustrated in FIG. 14. In this cross-section depiction, the body 92 includes a coupling platform 100 comprising a coupling 102 including a groove or slot onto which a corresponding coupling such as a clip, notch, tab, or other protrusion may be received. In this or other embodiments, the coupling 102 may incorporate magnets, magnet attractive materials, interlocking fastener structures such as touch fasteners, or other coupling configurations described herein. Similar to the embodiment described with respect to FIG. 9, the upper or lower rims 98, 99, which may correspond to a proximal and a distal rim in use, may also comprise a coupling 102 for use either together with or independently of the slot.

As introduced above, the anchor system 2 may include an anchor device including or configured to couple with a medical device. The medical device may be any device to be anchored to a target site within a biological lumen, such as those identified herein. In some embodiments, an anchor device 90 includes one or more coupling platforms 110 configured to couple to another coupling platform, such as coupling platforms associated with an embedment device or another anchor device. FIGS. 15-22B illustrate various embodiments of anchor devices 90 including a medical device 110. The anchor devices 90 include one or more coupling platforms 110 comprising one of more couplings 112 configured to couple to a corresponding coupling of another coupling platform, which may be a coupling platform 80 or variation thereof associated with an embedment device 10, such as those described with respect to FIGS. 7 & 8 and elsewhere herein, or a coupling platform 100 or variation thereof associated with an anchor device 90, such as those described with respect to FIGS. 9-14 and elsewhere herein.

Couplings 112 may generally be position along an outer perimeter of the body 92 or rim 98, 99, which may include a flange, for example. Example couplings 112 include projections, openings, slots, grooves, rails, latches, magnets, coupling surfaces, lips, ball, sockets, pins, clips, hooks, balls, or combinations thereof. Couplings 112 may include surfaces that may include textures, magnets, magnetized material, adhesives, interlocking structures or touch fasteners.

The anchor devices 90 illustrated in FIGS. 15-22B include medical devices 120 comprising gastric bypass stents. The stent includes a sleeve 122 having a proximal end 124 to anchor in the esophagus and a distal end 126 to position in the duodenum or beyond. The sleeve 122 will typically comprise an impermeable material that prevents passage of material between the interior lumen of the sleeve 122 and the exterior environment.

The medical device 120, or sleeve 122 in the illustrated embodiments, may be attached or otherwise coupled to the anchor device 90 comprising the coupling platform 110 using adhesives, fasteners, or other suitable technique. In one example, Velcro is used to couple the sleeve 122 to the anchor device 90.

Figure 15:
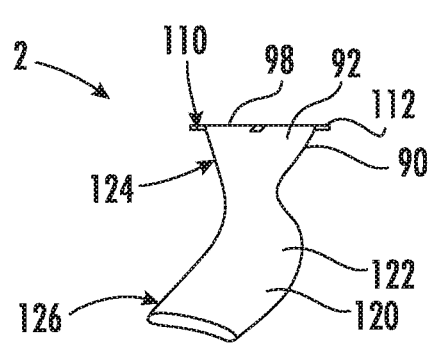
FIG. 15 illustrates an anchor device including a medical device according to various embodiments described herein.

The anchor device 90 device illustrated in FIG. 15 includes a coupling platform 110 including one or more couplings 112 comprising projections extending outwardly along a perimeter of the anchor device body 92, adjacent to an upper rim 98. The projections may be structured to be received within a coupling of another coupling platform, such as an opening, which may include a slot or groove, e.g., an opening of a coupling platform illustrated in FIGS. 7, 10, 14.

The projections may comprise metal, alloy, or polymer, such as silicones and plastics. The projections may be rigid to maintain coupling after being received within the opening. In some embodiments, one or more projections may be resiliently bendable or hinged such that the projections may be pulled past a surface defining an opening and thereafter project into the opening. In another embodiment, one or more projections may comprise a shape change or shape memory material such as nitinol. For example, the anchor device 90 may be delivered or otherwise positioned with respect to another coupling platform with the projection in a flexible or deformed state. When properly positioned relative to the opening, the projection may be induced to change or obtain a memory conformation wherein the projection projects into the opening. In some embodiments, the projections may comprise a coupling surface. The surface may include coupling features configured to assist in coupling or maintaining coupling such as adhesives, interlocking or touch fastener structures, e.g., hook-and-loop, suction or micro-suction structures, magnets or magnetic attractive materials. The coupling features may interact with surfaces of corresponding couplings such as surfaces defining openings, see, e.g., FIGS. 7, 10, 14, or surfaces such as a rim or other body surface, see, e.g., FIGS. 7-14, configured to couple to magnetic attractive materials or magnets of a coupling platform of an anchor device.

Figure 16:
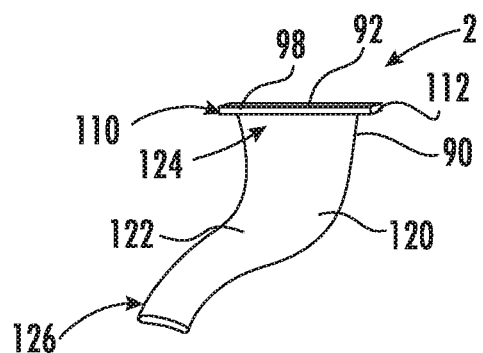
FIG. 16 illustrates an anchor device including a medical device according to various embodiments described herein.

The anchor device 90 device illustrated in FIG. 16 includes a coupling platform 110 including one or more couplings 112 comprising a flange extending outwardly along a perimeter of the anchor device body 92, adjacent to an upper rim 98. The flange may be structured to be received within a coupling of another coupling platform, such as an opening, which may include a slot or groove, e.g., an opening of a coupling platform illustrated in FIGS. 7, 10, 14. The flange may comprise metal, alloy, or polymer, such as silicones and plastics. The flange may be rigid to maintain coupling after being received within the opening. In some embodiments, multiple flanges may be positioned along the body 92. In one embodiment, the flange is resiliently bendable or hinged such that the flange may be pulled past a surface defining an opening and thereafter project into the opening. In another embodiment, the flange comprises a shape change or shape memory material such as nitinol. For example, the anchor device 90 may be delivered or otherwise positioned with respect to another coupling platform with the flange in a flexible or deformed state. When properly positioned relative to the opening, the flange may be induced to change or obtain a memory conformation wherein the flange projects into the opening. In some embodiments, the flange may comprise a coupling surface. The surface may include coupling features configured to assist in coupling or maintaining coupling such as adhesives, interlocking or touch fastener structures, e.g., hook-and-loop, suction or micro-suction structures, magnets or magnetic attractive materials. The coupling features may interact with surfaces of corresponding couplings such as surfaces defining openings, see, e.g., FIG. 7, 10, or 14, or surfaces such as a rim or other body surface, see, e.g., FIGS. 7-14, configured to couple to magnetic attractive materials or magnets of a coupling platform of an anchor device.

Figure 17:
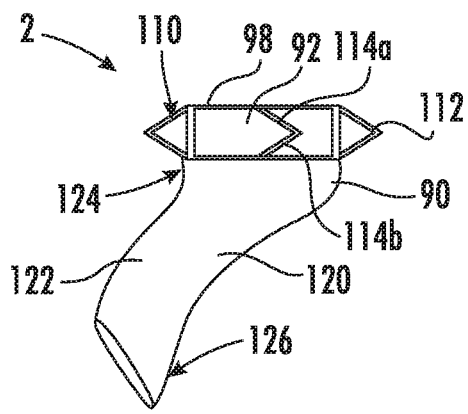
FIG. 17 illustrates an anchor device including a medical device according to various embodiments described herein.
Figure 18:
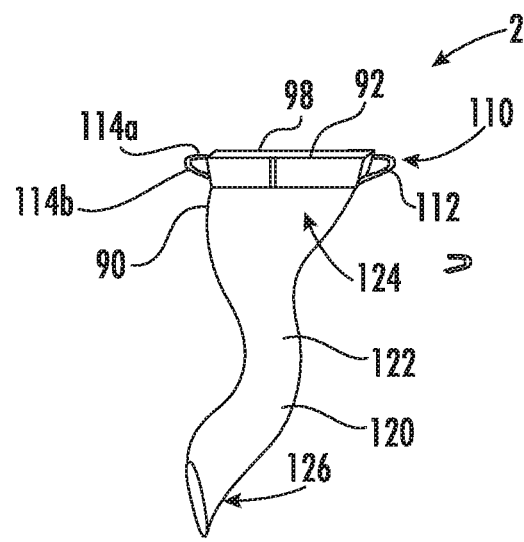
FIG. 18 illustrates an anchor device including a medical device according to various embodiments described herein.

The anchor devices 90 illustrated in FIGS. 17 & 18 each include a coupling platform 110 including one or more couplings 112 comprising projections. The projections include clips that extend outwardly from a perimeter of the implant device. The clips may comprise metal, alloy, or polymer. The clips may be resiliently bendable configured to compress inwardly and then decompress outwardly to extend into a corresponding opening of another coupling platform, see, e.g., FIGS. 7, 10, 14. For example, the coupling platforms 110 illustrated in FIGS. 17 & 18 may couple to a coupling platform of an embedment device or anchor device illustrated in FIG. 7, 10, or 14 by positioning clips into an opening of the respective coupling platform. In various embodiments, the clips may comprise stainless steel or a shape change or memory material such as nitinol configured to obtain a clip conformation to extend into an opening. The clips illustrated in FIG. 17 are positioned adjacent to an upper rim 98 and have a bend located substantially midway, longitudinally, between two legs 114a, 141b. The clips illustrated in FIG. 18 also include a bend located between two legs 114a, 114b but the bend is located more proximal to an upper leg 114a closest to the upper rim 98. In other embodiments, clips may include multiple bends. In some embodiments, the clips may be sized to press fit within openings to limit longitudinal, lateral, or rotational movement. In one example, clips are spaced apart to correspond with spacing of openings of corresponding couplings such that rotation is prevented by a boundary of one or more openings that couple to the clips.

Figure 19:
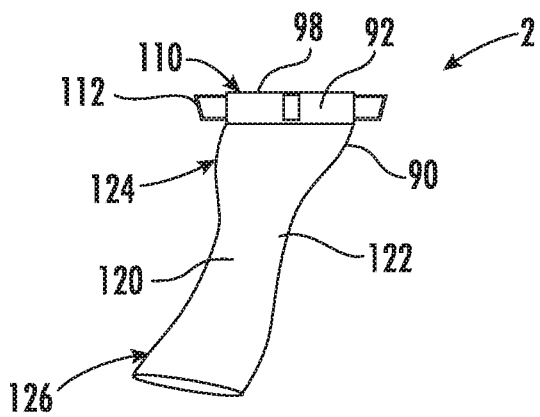
FIG. 19 illustrates an anchor device including a medical device according to various embodiments described herein.

The anchor device 90 device illustrated in FIG. 19 includes a coupling platform 110 including one or more couplings 112 comprising projections extending outwardly along a perimeter of the anchor device body 92. The projections may be structured to be received within a coupling of another coupling platform, such as an opening, which may include a slot or groove, e.g., an opening of a coupling platform illustrated in FIGS. 7, 10, 14. The projections may comprise metal, alloy, or polymer, such as silicones and plastics. The projections may be rigid in order to maintain coupling after being received within the opening. In some embodiments, the projections comprise a surface including coupling features configured to assist in coupling or maintaining coupling such as adhesives, interlocking or touch fastener structures, e.g., hook-and-loop, suction or micro-suction structures, magnets or magnetic attractive materials. The coupling features may interact with surfaces of corresponding couplings such as surfaces defining openings, see, e.g., FIGS. 7, 10, 14, or surfaces such as a rim or other body surface, see, e.g., FIGS. 7-14, configured to couple to magnetic attractive materials or magnets of a coupling platform of an anchor device.

In addition to the above or in a further example, the projections of the embodiment illustrated in FIG. 19 comprise biased tabs. The tabs may be biased outwardly of the perimeter of the body 92. For example, the tabs may be biased by a spring. In some embodiments, the tabs may be retracted and extended by actuating a linkage (not shown) coupled to the tabs to assist in coupling the coupling platform to another coupling platform in situ. In one example, a retainer may be used to maintain the tabs in a retracted position prior to coupling. A delivery device may be used to remove the retainer. In some embodiments, the retainer may release the tabs outwardly in response to an environmental condition or queue, which may include an induced electromagnetic or magnetic field, e.g., provided externally, by a delivery device, or by approximation with magnets or transmitter associated with the other coupling platform, such as with the corresponding coupling. Remote signaling, such as RFID may also be used to release the retainer is some embodiments.

The couplings 112 illustrated in FIGS. 15-19 include couplings 112 generally positioned along the perimeter of the body 92 and that are generally aligned along a single cross-section, transverse to the longitudinal axis of the implant device. In some embodiments, the coupling platform 110 may include multiple rows of couplings 112, staggered couplings 112, or couplings 112 located at different positions along the longitudinal length of the body 92. For example, multiple flanges or rows of clips may extend around the perimeter of the body 92. Coupling platforms 110 may also include one or more rows of coupling 112 that are positioned along different lengths of the body 92, such as a plurality of barbs arranged in a wave pattern around a perimeter of the anchor device, e.g., as described above with respect to FIG. 12 and below with respect to FIGS. 20A-22B.

Other coupling platform configurations may also be used. For example, a coupling platform may include a coupling comprising slot openings along a rim to receive a corresponding coupling comprising a projection of another coupling platform. The projections may be received through the slot and then translated along a path within the slot. In one embodiment, the slot may reduce in width or depth to achieve a compression fit. In another example, the slot may decrease in depth to compress the projection and then increase in depth at a sub-slot therealong to allow decompression of the projection into the sub-slot to couple the coupling platforms. In a further example, the projection is configured to be biased outwardly, such as the biased tabs described above with respect to FIG. 19. In a further example, the slot provides a twist-fit. In any of the above or another embodiment, the projection, slot, or both may include magnets to attract and couple to the corresponding coupling.

According to various embodiments, the anchor system includes a modular anchoring device. In one such embodiment, the anchor system also includes an embedment device. The anchor system may include one or more anchor devices wherein at least one of the anchor devices is configured to couple or be attached to a medical device. The anchor system may include a first anchor device configured to anchor to a tissue wall of a lumen that is embedded with an embedment device. The first anchor device may include anchors, e.g., as described herein, that penetrate tissue, interact via magnetism with the embedment device within the tissue or from a tissue surface, or combination thereof. In one embodiment, the first anchor device includes or is attached to a medical device. In another embodiment, the anchor system includes a second anchor device having a coupling platform configured to couple to a coupling platform of the first anchor device. The second anchor device may include, attach, or couple to a medical device. In a further embodiment, the embedment device includes a coupling platform and the first anchor device includes a coupling platform configured to couple to the coupling platform of the embedment device. The first anchor device may include, attach, or couple a medical device. In still a further embodiment, the first anchor device includes another coupling platform configured to couple to a coupling platform of the second anchor device wherein the second anchor device is includes, attaches, or couples the medical device. In any of the above embodiments, an anchor device may be configured to couple multiple anchor devices or medical devices. For example, an anchor device may couple a medical device utilizing a coupling platform described herein or may otherwise include various fittings for attaching one or medical devices prior to implantation of the anchor device.

Embedment and anchor devices including coupling platforms described herein may be configured for coupling, decoupling, or both in situ. Anchor devices may similarly be configured for anchoring to and removal from a tissue wall defining a biological lumen, which may be reinforced with an embedment device as described herein. Such configurations may beneficially allow ease of removal, repair, and replacement of anchor devices and medical devices. In some embodiments, an anchor device and an associated coupling platform may provide a platform for coupling and decoupling anchoring devices comprising medical devices on an as needed based. In one example, coupling platforms comprising coupling configurations corresponding to a coupling platform of an anchor device or embedded device may be fitted to multiple medical devices. Thus, medical devices may be conveniently removed, implanted, and interchanged as needed.

In various embodiments, the anchor system includes an anchor device including a medical device configured to be delivered to the target site together. In some embodiments, the anchor device and medical device are integrated such that it may not be practical to detach the medical device from the anchor device once implanted and anchored. For example, an integrated anchor and medical device may include a gastric bypass sleeve having an integrated anchor device comprising an inflatable balloon, e.g., such as described with respect to FIG. 13 wherein the sleeve may be sewn to or adhered with adhesive to the balloon.

Figure 20A:
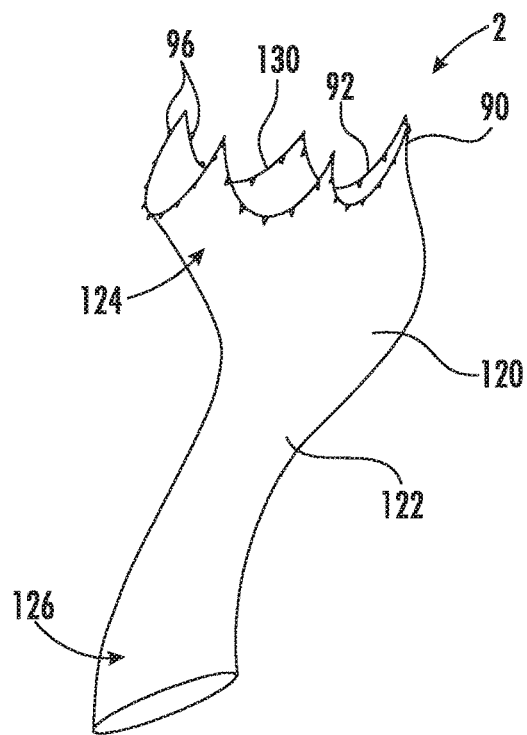
FIG. 20A illustrates an anchor device that includes a medical device according to various embodiments described herein.

FIG. 20A illustrates an embodiment of an anchor device 90 attached to a medical device 120 comprising a gastric sleeve 122 according to various embodiments. The anchor device 90 has a body 92 including a rim 130 having an annular cross-section an extending around a perimeter in a wave conformation. The body 92 may be to that of the anchor device described with respect to FIG. 12. For example, the rim may include a wire, such as a stainless steel or nitinol wire. A plurality of anchors 96 project from the rim 130. The anchors 96 may include projections, such as hooks, configured penetrate wall tissue reinforced with an embedded device to anchor thereto. For example, the embedded device may be an embedded device described herein, such as a mesh stent, e.g., a stainless steel or nitinol mesh stent, (see, e.g., FIG. 1), coil, e.g., a stainless steel or nitinol coil, (see, e.g., FIG. 2), injected polymer, expandable tubing, or implanted threaded wires. In various embodiments, the projections comprise barbs, hooks, or straight projections. The rim 130 is attached to a proximal end 134 of the sleeve 122. The sleeve 122 will typically comprise an impermeable material to maintain separation between the interior and exterior of the sleeve 122. In one embodiment, the sleeve 122 comprises ePTFE, however, other materials may be used. In one particular embodiment, the sleeve 122 comprises a 24 inch to 30 inch ePTFE impermeable sleeve. In other embodiments, the sleeve 122 may be longer or shorter. The sleeve 122 may attach to the body 92 of the anchor device 90 utilizing straps, adhesives, Velcro or other suitable method.

Figure 20B:
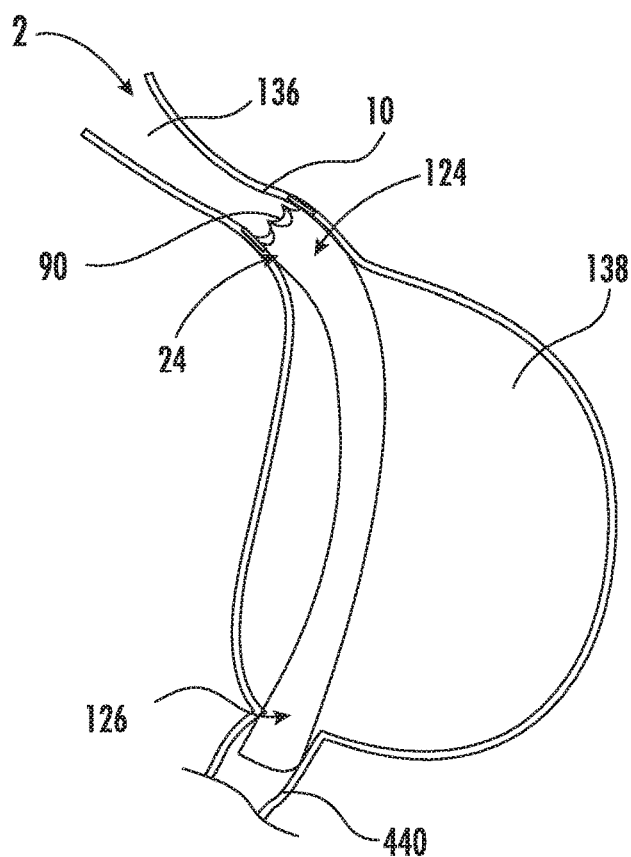
FIG. 20B illustrates the anchor device of FIG. 20A anchored within a biological lumen according to various embodiments described herein.

FIG. 20B illustrates the anchor device 90 and medical device 120 of FIG. 20A implanted in a biological lumen according to one method. The anchor device 90 and medical device 120 may be delivered into the esophagus utilizing a delivery device, which may be similar to the delivery device described with respect to FIG. 23. For example, the anchor device 90 and medical device 120 may be delivered endoscopically using fluoroscopy. The distal end 126 of the sleeve 122 may be passed through a delivery sheath through the esophagus 136, stomach 138, and then be delivered from the sheath into the duodenum 140. The anchor device 90 and proximal end 124 of the sleeve 122 may be delivered from the sheath into the esophagus 138. The anchor device 90 may include a delivery conformation including a reduced dimension for delivery, which may be similar to the delivery conformation described with respect to the embedment device. The anchor device 90 may transition or be manipulated into an anchor conformation at the target site 24. The anchors 96 may anchor to a tissue wall at the target site 24, which is reinforced with an embedment device 10. In one embodiment, the delivery system includes a capsule that may be actuated, e.g., pulled back, to act as a plunger. The anchor device 90 may be positioned in the capsule in a collapsed delivery conformation. The sleeve 122 may be delivered over a guide wire. When fully extended in the intestines, the capsule may be pulled back into the esophagus, and the anchor device 90 may be pushed out using the plunger, which may be actuated using a handle external to the patient.

Figure 21A:
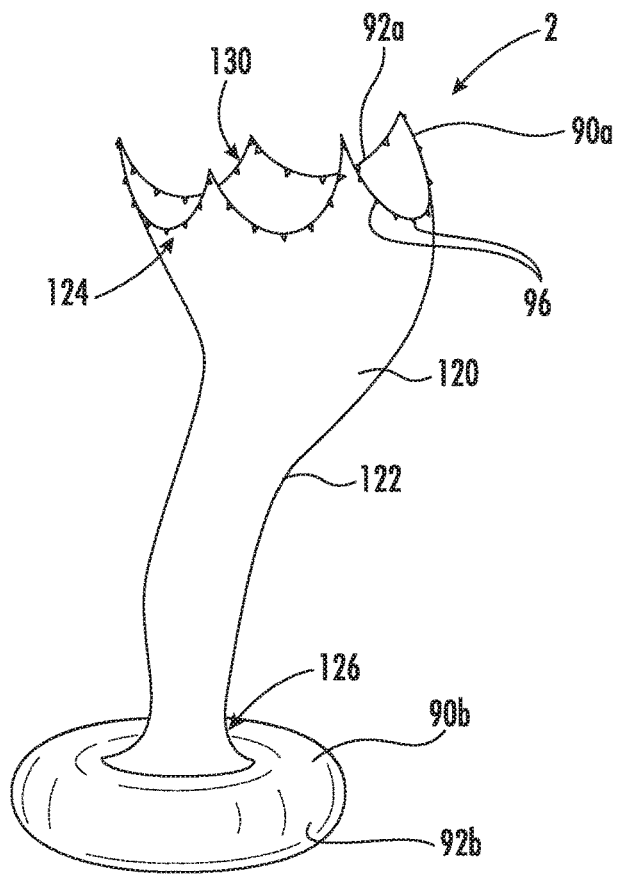
FIG. 21A illustrates a device comprising two anchor devices and a medical device according to various embodiments described herein.

In some embodiments, multiple anchor devices may be integrated with a medical device. For example, FIG. 21A illustrates two anchor devices 90a, 90b associated with a medical device 120 according to various embodiments described herein. The medical device 120 includes a gastric bypass sleeve 122 having a first anchor device 90a positioned along a first end (proximal end 124) and a second anchor device 90b positioned along a second end (distal end 126). In some embodiments, the first or second anchor device 90a, 90b may be positioned along a middle portion of the sleeve 122. Additional anchor devices may also be used. The first anchor device 90a includes a body 92a and is similar to the anchor device described with respect to FIGS. 12 & 20A. The second anchor device 90b includes a body 92b comprising a hollow cylinder or balloon similar to the anchor device described with respect to FIG. 13.

Figure 21B:
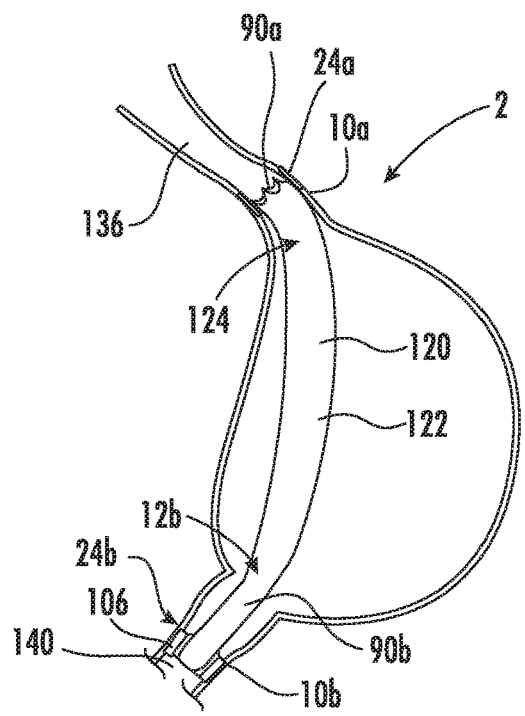
FIG. 21B illustrates the device of FIG. 21A anchored within a biological lumen according to various embodiments described herein.

FIG. 21B illustrates the anchor devices 90a, 90b and medical device 120 of FIG. 21A implanted in a biological lumen according to one method. The anchor devices 90a, 90b and medical device 120 may be delivered into the esophagus utilizing a delivery device, which may be similar to the delivery device described with respect to FIG. 23. The distal end 126 of the sleeve 122 including the second anchor device 90b may be passed through a delivery sheath extending through the esophagus 136, stomach 138, and then be delivered from the sheath into the duodenum 140. The first anchor device 90a and proximal end 124 of the sleeve 122 may be delivered from the sheath into the esophagus 138. The second anchor device 90b may be inflated from a deflated delivery conformation to transition to an anchor conformation at the target site 24b in the duodenum 140 resulting in outward force being applied against the tissue wall to thereby anchor the balloon. Thus, the application of outwardly directed force against the tissue wall prevents retrograde passage into the stomach. Additionally, in some embodiments, the configuration may not apply significant outward force in the anchor conformation, e.g., inflated, but does not permit retrograde passage into the stomach. For example, the anchor conformation may conform to one or more dimensions of the duodenum or otherwise obtain dimensions larger than the pylorus to prevent retrograde passage into the stomach. The first anchor device 90a may transition or be manipulated into an anchor conformation at the target site 24a. The anchors 96 may anchor to a tissue wall at the target site 24. In the illustrated embodiment, the tissue walls at both target sites 24a, 24b are reinforced with a respective embedment device 10a, 10b. In some embodiments, a second embedment device 10b is not used.

In various embodiments, the sleeve 122 may be strengthened or otherwise augmented to maintain stable positioning when implanted. For example, as described with respect to FIGS. 21A & B, additional anchor devices 90b may be employed to anchor multiple portions of the sleeve 122. Other anchor devices 90, such as those described herein, may also be used to anchor to the duodenum. For example, an additional anchor device 90b similar to the first anchor device 90a may be added to the middle or distal end of the sleeve 122 keep the sleeve 122 in the duodenum.

In some embodiments, passages for gastric acid or fluid may be formed through the sleeve 122, between the second anchor device 90b and the wall of the duodenum, or between the second anchor device 90b and the sleeve 122. For example, in various embodiments, a second anchor device 90b engages an embedment device 10b or anchor device anchored along the embedment device 10b to effectively couple thereto as described herein. The second anchor device 90b may anchor via projections such as hooks or other coupling platform that engages the tissue and embedded structure or a lumen projection thereof, which may include a coupling platform of another anchor device anchored along the embedment device 10b. In one such embodiment, spaces between these anchor points may provide passage for gastric fluid. For example, passages for gastric fluid may be provided between the second anchor device 90b and an anchor device to which it is anchored, the embedment device 10b and a lumen projection thereof, the second anchor device and the embedment device 10b, or the embedment device 10b and an anchor device to which the second anchor device 90b is anchored. In one embodiment, the second anchor device 90b or an anchor device to which it is anchored defines passages for gastric fluid.

Figure 22A:
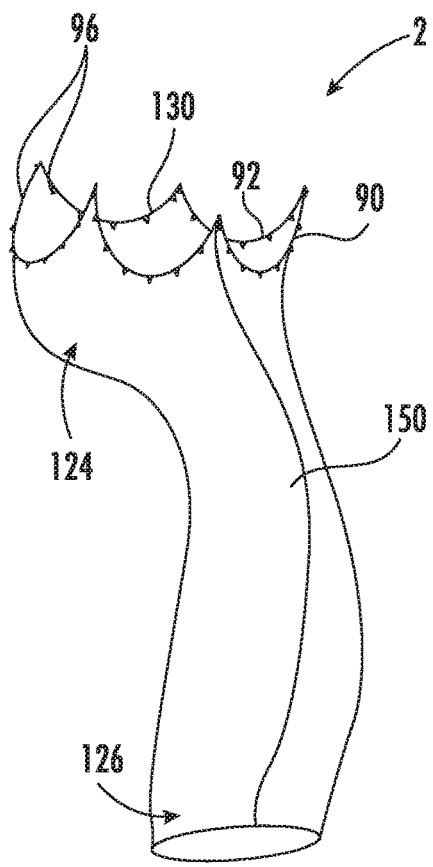
FIG. 22A illustrates an anchor device including a medical device according to various embodiments described herein.

FIG. 22A illustrates an anchor device 90 and medical device 120 according to various embodiments. The anchor device 90 and medical device 120 are similar to that described with respect to FIGS. 20A & 20B; however the bypass sleeve includes an embedded wire 150 extending along the sleeve 122. The wire 150 may comprise a metal or alloy such as stainless steel or nitinol. The wire 150 is fixed within the sleeve 122 and may be manipulated to a desired conformation to strengthen the stability and conformation of the sleeve 122. In a further embodiment, a wire 150 may be deployed with the sleeve 150 and subsequently ratcheted or snapped into place similar to a zip tie. In another embodiment, the wire 150 comprises a stiffing coil wire that coils around the sleeve 122. In yet another embodiment, the sleeve 122 may have embedded wire 150 comprising a plurality of rings. In still yet another embodiment, the sleeve 122 includes an embedded wire 150 comprises a stiffing coil configured to provide modification capabilities similar to corrugated tubing.

Figure 22B:
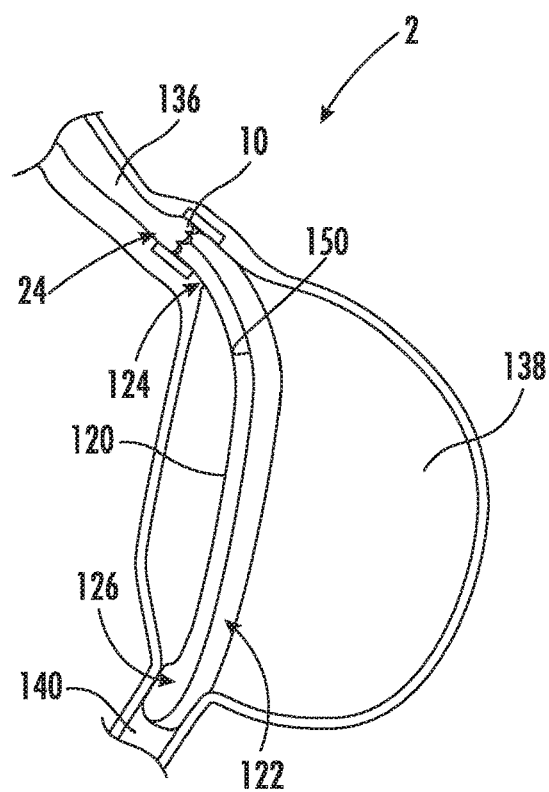
FIG. 22B illustrates the anchor device and medical device of FIG. 22A anchored within a biological lumen according to various embodiments described herein.

FIG. 22B illustrates the anchor device 90 and medical device 120 of FIG. 22A implanted in a biological lumen according to one method. The anchor device 90 and medical device 120 may be delivered into the esophagus utilizing a delivery device as described with respect to FIG. 20B. The stiffening wire 150 may be used to position or maintain position of the distal end 126 of the sleeve 122 within the duodenum 140.

While the illustrated anchor devices 90 generally include annular bodies that anchor or couple to the tissue or coupling platforms along multiple arcs forming the circumference of the wall, device, or lumen, in some embodiments, anchor devices 90 may attach to a tissue wall, device, or lumen only along a 15, 45, 90, or 180 arch. For example, an anchor device 90 may include any cross-sectional shape and may or may not include a central hole. An anchor device 90 may attach to or couple along only a portion of a circumference of the lumen.

It is to be appreciated that the anchor devices illustrated in FIGS. 9-14 may be configured with similar coupling platforms as described with respect to FIGS. 15-19 to couple to another coupling platform rather than anchor to a tissue wall, embedment device, or another anchor device anchored to a tissue wall or embedment device. It is also to be appreciated that the anchor devices illustrated in FIGS. 9-14 may also include medical devices in addition to or instead of coupling with coupling platforms of anchor devices comprising medical devices or that may further couple with anchor devices comprising medical devices. Further, the anchor devices 90 illustrated in FIGS. 15-22B may further include coupling platforms to also couple additional anchor devices. It is also to be appreciated, that coupling platforms described with respect to coupling two particular devices may be switched.

In various embodiments, the anchor device may produce an outwardly directed force against a reinforced tissue wall to assist in engagement of anchors or force driven anchoring. As noted above and elsewhere herein, the embedment device may prevent the reinforced wall from expanding away from outwardly directed force applied along the reinforced wall. The reinforced wall may provide a firm structure onto which the outwardly directed force may compress against to anchor along the reinforced wall. In one embodiment, an embedment device may be configured to provide different or differential rigidity to outwardly directed force. For example, the embedment device may include a contoured mesh or coil providing an area of reduced diameter compared to an adjacent reinforced area. In another example, an amount of polymer injected along a portion of the tissue wall is reduced relative to one or more adjacent regions. In another example, a depth or expandability of wire threaded along the tissue wall may be increased relative to one or more adjacent regions. In one example, the embedment device may be differentially expanded outwardly a distance that does not result in migration if the embedment device external of the tissue wall but that allows a pocket or groove to form along the wall into which an anchor or coupling thereof may position within. The pocket or groove may extend about an entire circumference of the wall or only along one or more portions thereof. In some embodiments, an anchor of an anchor device may position just proximal to the reinforced portion of the wall such that the outwardly directed force expands the wall outward relative to the reinforced portion of the wall. In one embodiment, the embedment device or devices may be embedded at two or more locations along the wall and therein provide a reinforced wall at the two or more locations. An anchor may be located between the two or more locations and therebetween provide outwardly directed force to anchor along the reinforced wall between the two or more embedment devices or regions thereof. In some embodiments, the embedment device is flexible with respect to reduction in cross section to allow contraction of the tissue wall but rigid with respect to dilation beyond a maximum cross-section or perimeter, as described above with respect to limitation of migration. A positioning device may be used to embed a flexible configuration of an embedment device. Assisting embedment may also include heat, electrical current, wire shapes, or other embedment assisting features described herein.

In various embodiments, a method to reinforce a biological lumen, such as the gastrointestinal tract, includes embedding an embedment device comprising a reinforcing material or structure into an area of a tissue wall defining the lumen. The method may include embedding the embedment device in a manner so as to prevent expansion or otherwise strengthen the wall. The method may include delivering or embedding the embedment device endoscopically. Delivering or embedding the embedment device may include injecting a polymer, threading a wire or wires, or applying or delivering a device to apply outward force from within the lumen to cause wires or a mesh structure to embed via the outward force.

In various embodiments, the embedment device may be used to reinforce a tissue wall of a biological lumen. As described above and elsewhere herein, the reinforced tissue wall may therefore be strengthen for subsequent anchoring of devices. For example, the embedment device may be used to strengthen a tissue wall to allow anchoring devices, which may include implant devices, in the gastrointestinal tract for various reasons, including diagnostic, slow or speed transit, or bypass areas. In further embodiments, the embedment device may be used to reinforce a stomach from expanding after gastric reduction surgery, preventing esophageal dilation in patients with Achalasia. The reinforcement may strengthen the reinforced area to withstand peristaltic and other forces dragging on an implant anchored thereto. The embedment device may be further configured to allow or facilitate coupling, anchoring, or both.

Anchor devices for anchoring to the reinforced gastrointestinal tract may anchor via anchor mechanisms described herein. For example, anchor devices may anchor to a reinforced gastrointestinal tract via direct force. That is, the embedment device may prevent or limit the ability of the tissue walls along the reinforced portion of the lumen to expand away from the direct, outward, force. In one example, the anchor device may include magnets providing magnetic attraction to the embedment device where the embedded structure allows for stronger forces to be applied than the native structure could resist.

According to various embodiments, a method of reinforcing a biological lumen comprises positioning an embedment device at a target site wherein the embedment device applies outwardly directed force against a tissue wall defining the lumen. The embedment device may embed within the tissue wall. The embedment device may by implanted utilizing endoscopic techniques.

Numerous specific details are set forth herein to provide a thorough understanding of the overall structure, function, manufacture, and use of the embodiments as described in the specification and illustrated in the accompanying drawings. It will be understood by those skilled in the art, however, that the embodiments may be practiced without the specific details described and illustrated herein. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "in a further embodiment," "one embodiment," or "an embodiment" means that a particular feature, structure, or characteristic described in connection with the embodiment is included in at least one embodiment. Thus, appearances of the phrases "in various embodiments," "in some embodiments," "in a further embodiment," "in one embodiment," or "in an embodiment" in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute. Any numerical range recited herein includes all values from the lower value to the upper value. For example, if a range is stated as 1 to 50, it is intended that values such as 2 to 40, 10 to 30, or 1 to 3, etc., are expressly enumerated in this specification. These are only examples of what is intended, and all possible combinations of numerical values between and including the lowest value and the highest value enumerated are to be considered to be expressly stated in this application. With respect to numerical descriptions modified by approximately, the modified number is intended to include +/−10% of the identified number. Unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

What is claimed is:

1. A method of reinforcing a tissue wall of a gastrointestinal tract lumen for anchoring a medical device directly or indirectly to the reinforced tissue wall, the method comprising:

embedding a body of an embedment device into a portion of a tissue wall defining a gastrointestinal tract lumen, the body comprising a reinforcement material or structure that reinforces the portion of the tissue wall when embedded therein; and engaging the embedment device with one more anchor structures of an anchor device to anchor the anchor device within the lumen, wherein the anchor device does not completely overlap the body with a covered surface that applies outwardly directed pressure along the portion of the tissue wall sufficient to cause the body to unembed, and wherein the anchor device comprises a medical device or a platform to which a medical device is coupled or subsequently coupled in situ.

2. The method of claim 1, further comprising removing the anchor device and anchoring another anchor device or the same anchor device to the portion of the tissue wall.

3. The method of claim 1, wherein the medical device comprises a diagnostic device, therapeutic device, regulatory device, sensor device, separation device, or transport device.

4. The method of claim 1, wherein the medical device regulates and/or modifies flow of material within the lumen, detects and/or analyzes components of material within the lumen, releases medication and/or another therapeutic substances into the lumen, or observes or measures a condition and/or state within the lumen.

5. The method of claim 1, wherein engaging the embedded structure comprises penetrating the portion of the tissue wall with the one or more anchor structures to engage the body therein.

6. The method of claim 1, wherein embedding the body comprises delivering the embedment device into the lumen and applying outwardly directed force along an interior side of the portion of the tissue wall to embed the body therein.

7. The method claim 6, further comprising heating or conducting an electrical current through the reinforcement material or structure to assist in embedding the reinforcement material or structure of the body into the portion of the tissue wall.

8. The method claim 6, further comprising coating the material or structure with a chemical or biological substance to assist in embedding the reinforcement material or structure of the body into the portion of the tissue wall.

9. The method of claim 6, wherein the body of the embedment device defines a cross-section dimension greater than an initial corresponding cross-section dimension of the lumen to therein apply the outwardly directed force along the interior side of the portion of the tissue wall to embed therein.

10. The method of claim 9, wherein the cross-section dimension of the body is less than a corresponding cross-section dimension of the portion of the tissue wall and corresponding lumen, taken between exterior sides of the portion of the tissue wall, such that the body does not migrate to an exterior side of the portion of the tissue wall.

11. The method of claim 9, wherein the body comprises a wire mesh, and wherein the wire mesh includes one or more physical blocks extending between adjacent openings to prevent migration of the body to an exterior side of the portion of the tissue wall.

12. The method of claim 10, wherein the body of the embedment device comprises a wire coil or a wire mesh.

13. The method of claim 6, wherein the body of the embedment device comprises an expandable tubular structure, wherein the expandable tubular structure is expandable or biased to obtain a cross-section dimension greater than an initial corresponding cross-section dimension of the lumen to therein apply the outwardly directed force along the interior side of the portion of the tissue wall to embed therein.

14. The method of claim 13, wherein the expandable tubular structure comprises a wire mesh or coil.

15. The method of claim 6, wherein the body of the embedment device comprises a self-expanding tubular structure.

16. The method of claim 15, wherein the body of the embedment device has an embedding conformation and an embedded conformation, and wherein the body applies the outwardly directed force in the embedding conformation and discontinues application of the outwardly directed force in the embedded conformation.

17. The method of claim 16, wherein, in the embedded conformation, a cross-section dimension of the body is less than a corresponding cross-section dimension of the portion of the tissue wall and corresponding lumen, taken between exterior sides of the portion of the tissue wall, such that the body does not migrate to an exterior side of the portion of the tissue wall.

18. The method of claim 6, wherein applying the outwardly directed force along an interior side of the portion of the tissue wall comprises compressing the body against the interior side of the portion of the tissue wall.

19. The method of claim 18, wherein compressing the body against the interior side of the portion of the tissue wall comprises positioning an inflatable device within the lumen, interior of the reinforcement material or structure, and inflating the inflatable device such that the inflatable device obtains a cross-section sufficient to compress the body against the interior side of the portion of the tissue wall.

20. The method of claim 18, wherein compressing the body against the interior side of the portion of the tissue wall comprises applying a suction or negative pressure within the lumen.

21. The method of claim 6, further comprising delivering a positioning device into the lumen and positioning the positioning device within the lumen, interior of the reinforcement material or structure, to secure the body of the embedment device along the interior side of the portion of the tissue wall during the embedding, wherein the positioning device comprises one or more projections to penetrate the portion of the tissue wall but not puncture an exterior side of the portion of the tissue wall.

22. The method of claim 21, wherein the projections are attached to the body and comprise a projection selected from a dissolvable or absorbable barbs, hooks, or pins.

23. The method of claim 1, wherein the anchor device comprises a platform for in situ coupling of medical devices to anchor the medical devices within the gastrointestinal lumen, and wherein the method further comprises coupling a gastrointestinal bypass stent or sleeve to the anchor device in situ.

24. The method of claim 23, further comprising decoupling the gastrointestinal bypass stent or sleeve from the anchor device in situ and recoupling the gastrointestinal bypass stent or sleeve or another medical device to the anchor device in situ.

25. A method of reinforcing a tissue wall of a biological lumen, the method comprising:
    embedding a reinforcement material or structure into a portion of a tissue wall defining a gastrointestinal tract lumen, and wherein embedding the reinforcement material or structure comprises threading a wire along the portion of the tissue wall or injecting a polymer into the portion of the tissue wall; and
    anchoring an anchor device to the portion of the tissue wall, wherein the anchoring comprises penetrating into the tissue wall with the one more anchor structures of the anchor device and therein engaging the embedded reinforcement material or structure.

26. A method of reinforcing a tissue wall of a biological lumen, the method comprising:

embedding a reinforcement material or structure into a portion of a tissue wall defining a gastrointestinal tract lumen, wherein the reinforcement material or structure comprises an embedment device having a body, wherein embedding the reinforcement material or structure comprises delivering the embedment device into the lumen and applying outwardly directed force along an interior side of the tissue wall to embed the body therein;

delivering a positioning device into the lumen and positioning the positioning device within the lumen, interior of the reinforcement material or structure, to secure the body of the embedment device along the interior side of the tissue wall during the embedding, wherein the positioning device comprises a body and one or more projections, and wherein the one or more projections penetrate the tissue wall but not puncture an exterior side of the tissue wall; and anchoring an anchor device to the portion of the tissue wall, wherein the anchoring comprises penetrating into the tissue wall with the one more anchor structures of the anchor device and therein engaging the embedded reinforcement material or structure, wherein the body of the positioning device is absorbable or dissolvable or the method further comprises removing the positioning device after the embedment device has embedded the tissue wall.

* * * * *